(12) United States Patent
Fischer et al.

(10) Patent No.: US 7,612,079 B2
(45) Date of Patent: Nov. 3, 2009

(54) 2,6,9-SUBSTITUTED PURINE DERIVATIVES AND THEIR USE IN THE TREATMENT OF PROLIFERATIVE DISORDERS

(75) Inventors: Peter Martin Fischer, Angus (GB); Mike Jarman, London (GB); Ted McDonald, Reigate (GB); Bernard Nutley, Sutton (GB); Florence Raynaud, London (GB); Stuart Wilson, Sutton (GB); Paul Workman, Abinger Common (GB)

(73) Assignees: Cyclacel Limited, London (GB); Cancer Research Technology Limited, London (GB)

( * ) Notice: Subject to any disclaimer, the term of this patent is extended or adjusted under 35 U.S.C. 154(b) by 0 days.

(21) Appl. No.: 10/742,237

(22) Filed: Dec. 18, 2003

(65) Prior Publication Data

US 2005/0009846 A1    Jan. 13, 2005

Related U.S. Application Data

(63) Continuation of application No. PCT/GB02/02962, filed on Jun. 27, 2002.

(30) Foreign Application Priority Data

Jun. 27, 2001 (GB) .................... 0115713.0
Aug. 21, 2001 (GB) .................... 0120333.0

(51) Int. Cl.
*C07D 473/16* (2006.01)
*A61K 31/52* (2006.01)
*A61P 35/00* (2006.01)
*C07C 215/08* (2006.01)
*A61P 17/06* (2006.01)
*A61P 35/02* (2006.01)

(52) U.S. Cl. ............... 514/263.22; 514/263.4; 544/277; 564/321; 564/503

(58) Field of Classification Search ............ 514/263.22, 514/263.4; 544/277
See application file for complete search history.

(56) References Cited

U.S. PATENT DOCUMENTS

| | | | |
|---|---|---|---|
| 5,688,774 A | 11/1997 | Jacobson et al. | |
| 6,110,923 A | 8/2000 | Ely | |
| 6,255,485 B1 * | 7/2001 | Gray et al. | 544/277 |
| 6,316,456 B1 * | 11/2001 | Meijer et al. | 514/263.4 |
| 6,552,192 B1 * | 4/2003 | Hanus et al. | 544/280 |
| 6,573,044 B1 * | 6/2003 | Gray et al. | 435/6 |
| 6,790,958 B2 * | 9/2004 | Lum et al. | 544/277 |
| 6,949,644 B2 * | 9/2005 | Ding et al. | 544/277 |
| 2003/0191312 A1 * | 10/2003 | Ding et al. | 544/235 |
| 2003/0229105 A1 * | 12/2003 | Kashanchi | 514/263.2 |
| 2005/0256142 A1 * | 11/2005 | Fischer et al. | 514/263.22 |
| 2006/0183760 A1 * | 8/2006 | Fischer et al. | 514/263.22 |

FOREIGN PATENT DOCUMENTS

| | | |
|---|---|---|
| EP | 665229 B1 | 11/1999 |
| JP | 07-075798 | 3/1995 |
| WO | WO 90/09178 A1 | 8/1990 |
| WO | WO 93/17020 A2 | 9/1993 |
| WO | WO 93/17020 A3 | 9/1993 |
| WO | WO 97/16452 A1 | 5/1997 |
| WO | WO 97/20842 A1 | 6/1997 |
| WO | WO 98/16528 A1 | 4/1998 |
| WO | WO 99/07705 A1 | 2/1999 |
| WO | WO 99/34018 A1 | 7/1999 |
| WO | WO 99/43676 A2 | 9/1999 |
| WO | WO 00/44750 A1 | 8/2000 |
| WO | WO 00/55161 A1 | 9/2000 |

OTHER PUBLICATIONS

Prerna Diwan et al., J Virol. Sep. 2004; 78(17): 9352-9365.*
Thais M. Sielecki, J. Med. Chem. 2000; 43(1) pp. 1-18.*
Voskoglou-Nomikos et al. Clin. Cancer Res. 9(11):4227-39, 2003.*
Abraham et al. "Cellular effects of olomoucine, an inhibitor of cyclin-dependent kinases." *Biol. Cell.* 1995;83(2-3):105-20.
Chang et al. "Synthesis and application of functionally diverse 2,6,9-trisubstituted purine libraries as CDK inhibitors." *Chem. Biol.* Jun. 1999;6(6):361-75.
De Azevedo et al. "Inhibition of cyclin-dependent kinases by purine analogues: crystal structure of human cdk2 complexed with roscovitine." *Eur. J. Biochem.* Jan. 15, 1997;243(1-2):518-26.

(Continued)

*Primary Examiner*—Mark L Berch
(74) *Attorney, Agent, or Firm*—Lahive & Cockfield, LLP; Cynthia L. Kanik; Brian C. Trinque

(57) ABSTRACT

The present invention relates to compounds of formula I

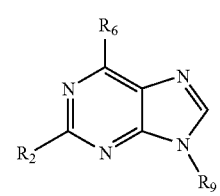

or a pharmaceutically acceptable salt thereof wherein
$R_2$ is 2-hydroxymethylpyrrolidin-1-yl, or $NHCH(R_4)CH(R_3)$OH, wherein $R_3$ is hydrogen or methyl and $R_4$ is methyl, ethyl or isopropyl;
$R_6$ is 3-nitrophenylamino, 3,4-dimethoxybenzylamino, 3-iodobenzyl-amino, pyrid-2-yl-methylamino, pyrid-4-yl-methylamino or indan-5-amino;
$R_9$ is isopropyl or cyclopentanyl.

In a further aspect, the invention relates to pharmaceutical compositions comprising said compounds, and the use thereof in treating antiproliferative disorders and or viral disorders.

22 Claims, No Drawings

OTHER PUBLICATIONS

Ducrot et al. "3D-QSAR CoMFA on cyclin-dependent kinase inhibitors." *J. Med. Chem.* Nov. 2, 2000;43(22):4098-108.

Fukatsu et al. "Synthesis of "reversed" nucleosides of some purine and pyrimidine bases." *Bulletin of the Chemical Society of Japan* 1973;46:3165-8.

Giocanti et al. "In vitro evaluation of a novel 2,6,9-trisubstituted purine acting as a cyclin-dependent kinase inhibitor." *Ann. N.Y. Acad. Sci.* 1999;886:180-2.

Gray, et al. "Exploiting chemical libraries, structure, and genomics in the search for kinase inhibitors." *Science.* Jul. 24, 1998;281(5376):533-8.

Gray, et al. "ATP-site directed inhibitors of cyclin-dependent kinases." *Curr. Med. Chem.* Sep. 1999;6(9):859-75.

Havlíček et al. "Cytokinin-derived cyclin-dependent kinase inhibitors: synthesis and cdc2 inhibitory activity of olomoucine and related compounds." *J. Med. Chem.* 1997;40(4):408-12.

Holy "Synthesis of enantiomeric N-(3-hydroxy-2-phosphonomethoxypropyl) derivatives of purine and pyrimidine bases." *Collect. Czech. Chem. Commun.* 1993;58:649-74.

Imbach et al. "2,6,9-trisubstituted purines: optimization towards highly potent and selective CDK1 inhibitors." *Bioorg. Med. Chem. Lett.* Jan. 4, 1999;9(1):91-6.

Legraverend et al. "Synthesis of C2 alkynylated purines, a new family of potent inhibitors of cyclin-dependent kinases." *Bioorg. Med. Chem. Lett.* Apr. 7, 1998;8(7):793-8.

Legraverand et al. "Synthesis and in vitro evaluation of novel 2,6,9-trisubstituted purines acting as cyclin-dependent kinase inhibitors." *Bioorg. Med. Chem.* 1999;7(7):1281-93.

Meijer et al. "Biochemical and cellular effects of roscovitine, a potent and selective inhibitor of the cyclin-depenedent kinases cdc2, cdk2 and cdk5." *Eur. J. Biochem.* 1997;243(1-2):527-36.

Oh et al. "Synthesis and biological activities of C-2, N-9 substituted 6-benzylaminopurine derivatives as cyclin-dependent kinase inhibitor." *Arch. Pharm.* (Weinheim). Jun. 1999;332(6):187-90.

Rudolph et al. "Activation of cyclin-dependent kinases by Myc mediates induction of cyclin A, but not apoptosis." *EMBO J.* Jun. 17, 1996;15(12):3065-76.

Schow et al. "Synthesis and activity of 2,6,9-trisubstituted purines." *Bioorg. Med. Chem. Lett.* 1997;7(21):2697-702.

Tao et al. "Inhibitors of cytokinin metabolism III. The inhibition of cytokinin N-glucosylation in radish cotyledons." *J. Plant Growth Regul.* 1991;10:179-85.

Veeranne "Inhibition of neuronal cyclin-dependent kinase-5 by staurosporine and purine analogs is independent of activation by Munc-18." *Neurochem. Res.* May 1996;21(5):629-36.

Vesely et al. "Inhibition of cyclin-dependent kinases by purine analogues." *Eur. J. Biochem.* Sep. 1, 1994;224(2):771-86.

\* cited by examiner

2,6,9-SUBSTITUTED PURINE DERIVATIVES AND THEIR USE IN THE TREATMENT OF PROLIFERATIVE DISORDERS

RELATED APPLICATIONS

This application is a continuation of PCT/GB02/02962, which was filed on Jun. 27, 2002, and which claims priority to GB 0120333.0, which was filed on Aug. 21, 2001, and GB 0115713.0, which was filed on Jun. 27, 2001. The entire contents of each of these applications are hereby incorporated herein by reference.

The present invention relates to new 2,6,9-substituted purine derivatives and their biological applications. In particular, the invention relates to purine derivatives having antiproliferative properties which are useful in the treatment of proliferative disorders such as cancer, leukemia, psoriasis and the like.

BACKGROUND OF THE INVENTION

Initiation, progression, and completion of the mammalian cell cycle are regulated by various cyclin-dependent kinase (CDK) complexes, which are critical for cell growth. These complexes comprise at least a catalytic (the CDK itself) and a regulatory (cyclin) subunit. Some of the more important complexes for cell cycle regulation include cyclin A (CDK 1—also known as cdc2, and CDK2), cyclin B1-B3 (CDK1), cyclin C (CDK8), cyclin D1-D3 (CDK2, CDK4, CDK5, CDK6), cyclin E (CDK2), cyclins K and T (CDK9) and cyclin H (CDK7). Each of these complexes is involved in a particular phase of the cell cycle.

The activity of CDKs is regulated post-translationally, by transitory associations with other proteins, and by alterations of their intracellular localisation. Tumour development is closely associated with genetic alteration and deregulation of CDKs and their regulators, suggesting that inhibitors of CDKs may be useful anti-cancer therapeutics. Indeed, early results suggest that transformed and normal cells differ in their requirement for e.g. cyclin A/CDK2 and that it may be possible to develop novel antineoplastic agents devoid of the general host toxicity observed with conventional cytotoxic and cytostatic drugs.

The function of CDKs is to phosphorylate and thus activate or deactivate certain proteins, including e.g. retinoblastoma proteins, lamins, histone H1, and components of the mitotic spindle. The catalytic step mediated by CDKs involves a phospho-transfer reaction from ATP to the macromolecular enzyme substrate. Several groups of compounds (reviewed in e.g. N. Gray, L. Détivaud, C. Doerig, L. Meijer, *Curr. Med. Chem.* 1999, 6, 859) have been found to possess anti-proliferative properties by virtue of CDK-specific ATP antagonism.

WO 98/05335 (CV Therapeutics Inc) discloses 2,6,9-trisubstituted purine derivatives that are selective inhibitors of cell cycle kinases. Such compounds are useful in the treatment of autoimmune disorders, e.g. rheumatoid arthritis, lupus, type I diabetes, multiple sclerosis; treating cancer, cardiovascular disease, such as restenosis, host v graft disease, gout, polycystic kidney disease and other proliferative diseases whose pathogenesis involves abnormal cell proliferation.

WO 99/07705 (The Regents of the University of California) discloses purine analogues that inhibit inter alia protein kinases, G-proteins and polymerases. More specifically, the invention relates to methods of using such purine analogues to treat cellular proliferative disorders and neurodegenerative diseases.

WO 97/20842 (CNRS) also discloses purine derivatives displaying antiproliferative properties which are useful in treating cancer, psoriasis, and neurodegenerative disorders.

SUMMARY OF THE INVENTION

The present invention seeks to provide new 2,6,9-substituted purine derivatives, particularly those having antiproliferative properties.

In a first aspect, the present invention relates to a compound of formula I

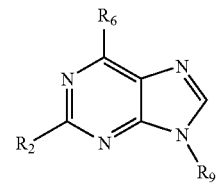

or a pharmaceutically acceptable salt thereof wherein $R_2$ is 3-hydroxypiperidin-1-yl, or $NHCH(R_4)CH(R_3)OH$, wherein $R_3$ is hydrogen or methyl and $R_4$ is methyl, ethyl or isopropyl;

$R_6$ is 3-nitrophenylamino, 3,4-dimethoxybenzylamino, pyrid-2-yl-methylamino, pyrid-4-yl-methylamino or indan-5-amino; and $R_9$ is isopropyl or cyclopentanyl.

In a preferred embodiment, $R_2$ is $NHCH(CHMe_2)CH_2OH$ or $NHCH(CH_2Me)CH_2OH$.

In an even more preferred embodiment of the invention, the compound of formula I is selected from the following:

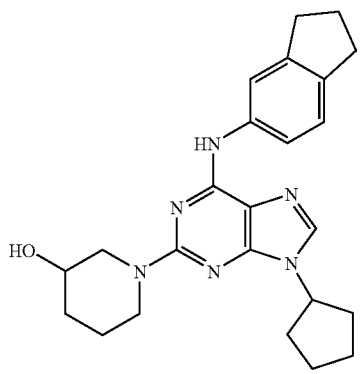

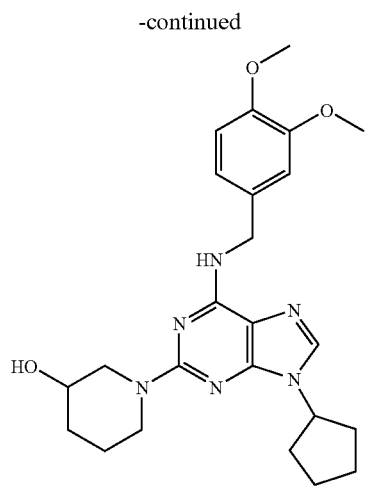
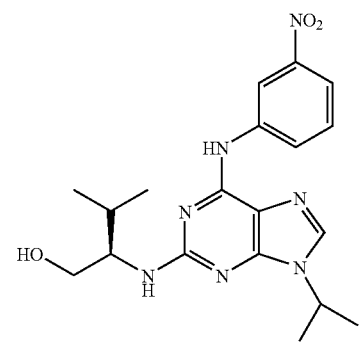
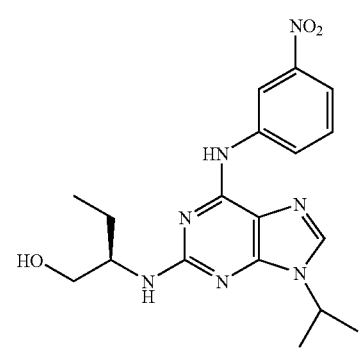
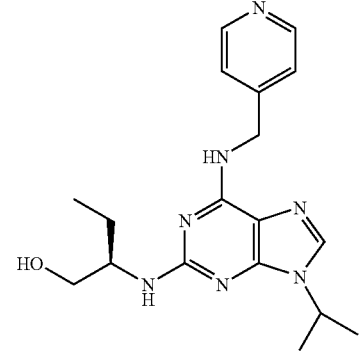
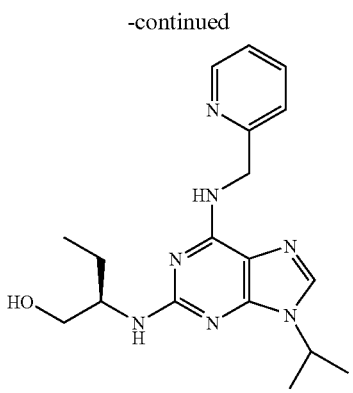
In another aspect, the invention relates to a compound selected from the following:
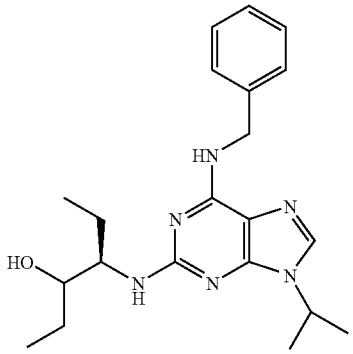
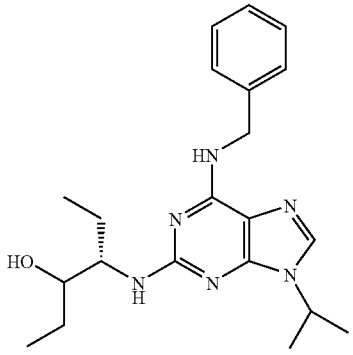
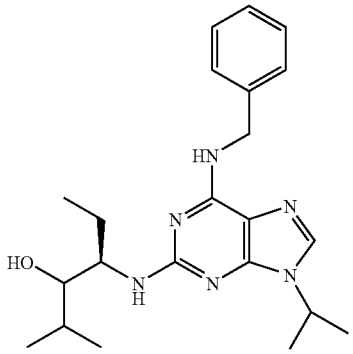

-continued

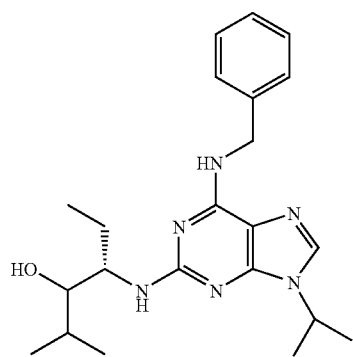

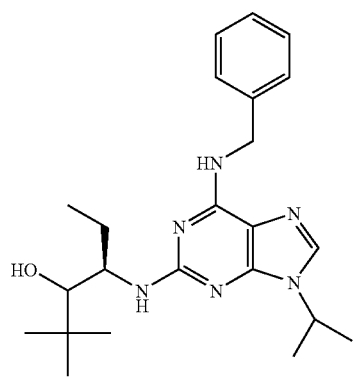

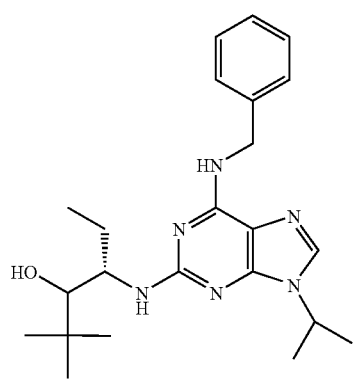

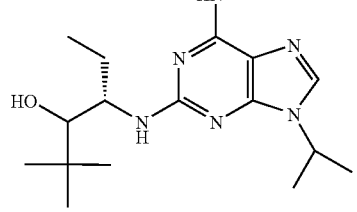

-continued

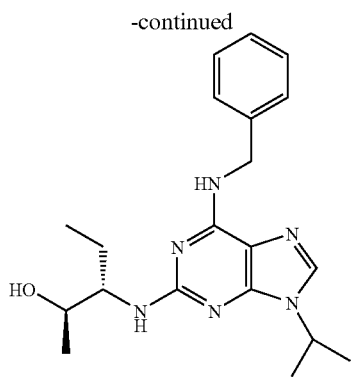

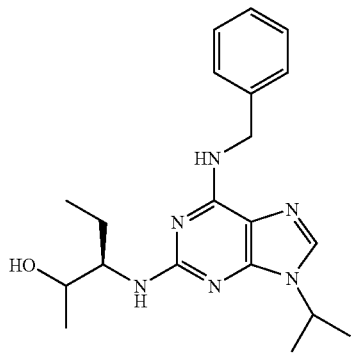

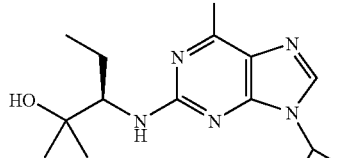

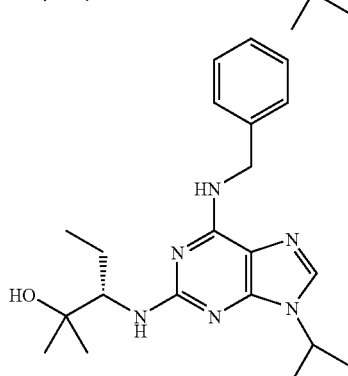

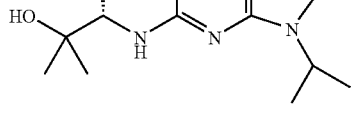

or a pharmaceutically acceptable salt thereof.

In one particularly preferred embodiment, the invention relates to an optical isomer of a compound as described hereinbefore.

As used herein, the term "optical isomer" is synonymous with the term "enantiomer" and refers to a molecule having a chiral centre which can exist in two different isomeric (so-called "enantiomeric") forms, each enantiomer being a mirror image of the other. The two possible forms are known as dextrorotatory (+) and laevorotatory (−), with each form rotating the plane of polarised light in opposite directions by an equal amount.

Thus, when $R_2$ is $NHCH(R_4)CH(R_3)$, $R_2$ may exist in one or more of the following conformations, or mixtures thereof:

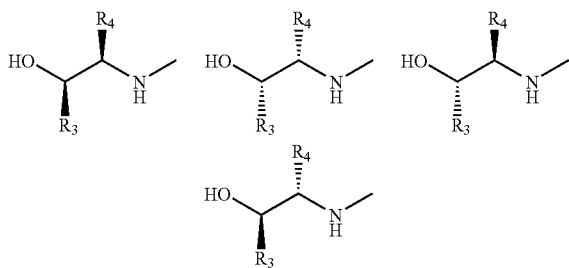

Likewise, when $R_2$ is 3-hydroxypiperidin-1-yl, $R_2$ may exist in one or more of the following conformations, or mixtures thereof:

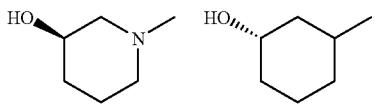

In another particularly preferred embodiment, the compound of the invention is in the form of a racemate.

As used herein, the term "racemate" refers to a mixture of equal quantities of the (+) and (−) enantiomers of an optically active compound. Such a mixture exhibits no optical activity, i.e. it does not rotate the plane of polarized light. The skilled person will appreciate that compounds of the invention containing more than one chiral centre may exist as two different stereoisomers, each of which may exist in two enantiomeric forms.

A second aspect provides a pharmaceutical composition comprising a compound of the present invention with a pharmaceutically acceptable diluent, excipient or carrier, or a mixture thereof.

A third aspect relates to the use of a compound of the present invention for treating a proliferative disorder.

Even more preferably the proliferative disorder is cancer or leukaemia.

In one particularly preferred embodiment, the proliferative disorder is psoriasis.

In an even more preferred embodiment of the invention, the compound is administered in an amount sufficient to inhibit at least one CDK enzyme.

Even more preferably, the CDK enzyme is CDK2.

In a fourth aspect, the invention relates to the use of a compound of the invention as an anti-mitotic agent.

Mitosis is the process by which the body grows and replaces cells. Mitosis refers to the indirect division of a cell, consisting of a complex of various processes, by means of which the two daughter nuclei normally receive identical complements of the number of chromosomes characteristic of the somatic cells of the species. Mitosis is divided into four phases: prophase, metaphase, anaphase and telophase.

The term "mitosis" is generally used interchangeably with cell division, but strictly speaking it refers to nuclear division, whereas cytokinesis refers to division of the cytoplasm.

As used herein, the term "anti-mitotic agent" refers to an agent which inhibits or prevents mitosis and/or cytokinesis.

In a fifth aspect, the invention relates to the use of a compound of the present invention for treating a neurodegenerative disorder. Typically, neurodegenerative disorders include central nervous system disorders characterised by a gradual and progressive loss of neural tissue. Examples include Alzheimer's disease and Parkinson's disease.

Even more preferably, the compound of the invention is used for treating neuronal apoptosis.

A sixth aspect relates to the use of a compound of the invention as an antiviral agent.

For this aspect, the compound of the invention is preferably administered in an amount sufficient to inhibit one or more of the host cell CDKs involved in viral replication, i.e. CDK2, CDK7, CDK8, and CDK9 [Wang D, De la Fuente C, Deng L, Wang L, Zilberman I, Eadie C, Healey M, Stein D, Denny T, Harrison L E, Meijer L, Kashanchi F. Inhibition of human immunodeficiency virus type 1 transcription by chemical cyclin-dependent kinase inhibitors. J. Virol. 2001; 75: 7266-7279].

In one particularly preferred embodiment, the compound of the invention may be used to treat one or more viral-related diseases, such as human cytomegalovirus (HCMV), herpes simplex virus type 1 (HSV-1), human immunodeficiency virus type 1 (HIV-1), and varicella zoster virus (VZV).

A seventh aspect relates to the use of a compound of the present invention in the preparation of a medicament for treating a proliferative disorder.

In a particularly preferred embodiment, the proliferative disorder is cancer or leukaemia.

As used herein the phrase "preparation of a medicament" includes the use of a compound of the invention directly as the medicament in addition to its use in a screening programmed for the identification of further agents or in any stage of the manufacture of such a medicament.

An eighth aspect relates to the use of a compound of the present invention for inhibiting a protein kinase.

In a preferred embodiment, the protein kinase is a cyclin dependent kinase, even more preferably CDK2.

A ninth aspect, the invention provides a method of treating a proliferative disease, said method comprising administering to a mammal a therapeutically effective amount of a compound of the invention.

It is to be appreciated that all references herein to treatment include one or more of curative, palliative and prophylactic treatment. Preferably, the term treatment includes at least curative treatment and/or palliative treatment.

Preferably, said proliferative disorder is cancer or leukaemia.

Even more preferably, the compound of the invention is administered orally.

A tenth aspect of the invention relates to a method of inhibiting a protein kinase, said method comprising contacting said protein kinase with a compound of the invention.

As mentioned hereinabove, preferably said protein kinase is a cyclin dependent kinase, even more preferably CDK2.

DETAILED DESCRIPTION OF THE INVENTION

Stereo and Geometric Isomers

Some of the compounds may exist as stereoisomers and/or geometric isomers, e.g. they may possess one or more asymmetric and/or geometric centres and so may exist in two or more stereoisomeric and/or geometric forms. The present invention contemplates the use of all the individual stereoisomers and geometric isomers of those compounds, and mixtures thereof. The terms used in the claims encompass these forms, provided said forms retain the appropriate functional activity (though not necessarily to the same degree).

Solvates

The present invention also includes the use of solvate forms of the compound of the present invention, including hydrates. The terms used in the claims encompass these forms.

Polymorphs

The invention furthermore relates to the compounds of or of use in the present invention (first and seconds aspects) in their various crystalline forms, polymorphic forms and (an) hydrous forms. It is well established within the pharmaceutical industry that chemical compounds may be isolated in any of such forms by slightly varying the method of purification and or isolation form the solvents used in the synthetic preparation of such compounds.

Pro-Drugs

As indicated, the present invention also includes the use of pro-drug forms of the compounds of the present invention. The terms used in the claims encompass these forms. Examples of prodrugs include entities that have certain protected group(s) and which may not possess pharmacological activity as such, but may, in certain instances, be administered (such as orally or parenterally) and thereafter metabolised in the body to form the compounds of the present invention which are pharmacologically active.

It will be further appreciated that certain moieties known as "pro-moieties", for example as described in "Design of Pro-drugs" by H. Bundgaard, Elsevier, 1985 (the disclosured of which is hereby incorporated by reference), may be placed on appropriate functionalities of the compounds. Such prodrugs are also included within the scope of the invention.

Mimetic

In one embodiment of the present invention, the compound may be a compound mimetic. As used herein, the term "mimetic" relates to any chemical which includes, but is not limited to, a peptide, polypeptide, antibody or other organic chemical which has the same qualitative activity or effect as a reference agent.

Pharmaceutical Salts

The compounds of the present invention may be administered as pharmaceutically acceptable salts. Typically, a pharmaceutically acceptable salt may be readily prepared by using a desired acid or base, as appropriate. The salt may precipitate from solution and be collected by filtration or may be recovered by evaporation of the solvent.

Pharmaceutically-acceptable salts are well known to those skilled in the art, and for example include those mentioned by Berge et al, in J. Pharm. Sci., 66, 1-19 (1977). Suitable acid addition salts are formed from acids which form non-toxic salts and include the hydrochloride, hydrobromide, hydroiodide, nitrate, sulphate, bisulphate, phosphate, hydrogenphosphate, acetate, trifluoroacetate, gluconate, lactate, salicylate, citrate, tattrate, ascorbate, succinate, maleate, fumarate, gluconate, formate, benzoate, methanesulphonate, ethanesulphonate, benzenesulphonate and p-toluenesulphonate salts.

When one or more acidic moieties are present, suitable pharmaceutically acceptable base addition salts can be formed from bases which form non-toxic salts and include the aluminium, calcium, lithium, magnesium, potassium, sodium, zinc, and pharmaceutically-active amines such as diethanolamine salts.

In addition, the compounds of the present invention may contain one or more asymmetric carbon atoms and therefore exists in two or more stereoisomeric forms. The present invention includes the individual stereoisomers of the compound and, where appropriate, the individual tautomeric forms thereof, together with mixtures thereof.

Separation of diastereoisomers may be achieved by conventional techniques, e.g. by fractional crystallisation, chromatography or H.P.L.C. of a stereoisomeric mixture of the agent or a suitable salt or derivative thereof. An individual enantiomer of the compound may be prepared from a corresponding optically pure intermediate or by resolution, such as by H.P.L.C. of the corresponding racemate using a suitable chiral support or by fractional crystallisation of the diastereoisomeric salts formed by reaction of the corresponding racemate with a suitable optically active acid or base, as appropriate.

The present invention also includes all suitable isotopic variations of the compound or a pharmaceutically acceptable salt thereof. An isotopic variation of an compound of the present invention or a pharmaceutically acceptable salt thereof is defined as one in which at least one atom is replaced by an atom having the same atomic number but an atomic mass different from the atomic mass usually found in nature. Examples of isotopes that can be incorporated into the compound and pharmaceutically acceptable salts thereof include isotopes of hydrogen, carbon, nitrogen and oxygen, such as $^{2}H$, $^{3}H$, $^{13}C$, $^{14}C$, $^{15}N$, $^{17}O$ and $^{18}O$ respectively. Certain isotopic variations of the compound and pharmaceutically acceptable salts thereof, for example, those in which a radioactive isotope such as $^{3}H$ or $^{14}C$ is incorporated, are useful in drug and/or substrate tissue distribution studies. Tritiated, i.e., $^{3}H$, and carbon-14, i.e., $^{14}C$, isotopes are particularly preferred for their ease of preparation and detectability. Further, substitution with isotopes such as deuterium, i.e., $^{2}K$, may afford certain therapeutic advantages resulting from greater metabolic stability, for example, increased in vivo half-life or reduced dosage requirements and hence may be preferred in some circumstances. Isotopic variations of the compound of the present invention and pharmaceutically acceptable salts thereof of this invention can generally be prepared by conventional procedures using appropriate isotopic variations of suitable reagents.

The present invention also includes (wherever appropriate) the use of zwitterionic forms of the compounds of the present invention.

The terms used in the claims encompass one or more of the forms just mentioned.

Formulation

The component(s) of the present invention may be formulated into a pharmaceutical composition, such as by mixing with one or more of a suitable carrier, diluent or excipient, by using techniques that are known in the art.

Pharmaceutical Compositions

The present invention provides a pharmaceutical composition comprising a therapeutically effective amount of one or more compounds and a pharmaceutically acceptable carrier, diluent or excipient (including combinations thereof).

The pharmaceutical compositions may be for human or animal usage in human and veterinary medicine and will typically comprise any one or more of a pharmaceutically acceptable diluent, carrier, or excipient. Acceptable carriers or diluents for therapeutic use are well known in the pharmaceutical art, and are described, for example, in Remington's Pharmaceutical Sciences, Mack Publishing Co. (A. R Gennaro edit. 1985). The choice of pharmaceutical carrier, excipient or diluent can be selected with regard to the intended route of administration and standard pharmaceutical practice. The pharmaceutical compositions may comprise as—or in addition to—the carrier, excipient or diluent any suitable binder(s), lubricant(s), suspending agent(s), coating agent(s), solubilising agent(s).

Examples of suitable carriers include lactose, starch, glucose, methyl cellulose, magnesium stearate, mannitol, sorbitol and the like. Examples of suitable diluents include ethanol, glycerol and water.

Examples of suitable binders include starch, gelatin, natural sugars such as glucose, anhydrous lactose, free-flow lactose, beta-lactose, corn sweeteners, natural and synthetic gums, such as acacia, tragacanth or sodium alginate, carboxymethyl cellulose and polyethylene glycol.

Examples of suitable lubricants include sodium oleate, sodium stearate, magnesium stearate, sodium benzoate, sodium acetate, sodium chloride and the like.

Preservatives, stabilizers, dyes and even flavoring agents may be provided in the pharmaceutical composition. Examples of preservatives include sodium benzoate, sorbic acid and esters of p-hydroxybenzoic acid. Antioxidants and suspending agents may be also used.

There may be different composition/formulation requirements dependent on the different delivery systems. By way of example, the pharmaceutical composition of the present invention may be formulated to be administered using a minipump or by a mucosal route, for example, as a nasal spray or aerosol for inhalation or ingestable solution, or parenterally in which the composition is formulated by an injectable form, for delivery, by, for example, an intravenous, intramuscular or subcutaneous route. Alternatively, the formulation may be designed to be administered by a number of routes.

Administration

The components of the present invention may be administered alone but will generally be administered as a pharmaceutical composition—e.g. when the components are in admixture with a suitable pharmaceutical excipient, diluent or carrier selected with regard to the intended route of administration and standard pharmaceutical practice.

For example, the composition can be administered (e.g. orally or topically) in the form of tablets, capsules, ovules, elixirs, solutions or suspensions, which may contain flavouring or colouring agents, for immediate-, delayed-, modified-, sustained-, pulsed- or controlled-release applications.

If the pharmaceutical composition is a tablet, then the tablet may contain excipients such as microcrystalline cellulose, lactose, sodium citrate, calcium carbonate, dibasic calcium phosphate and glycine, disintegrants such as starch (preferably corn, potato or tapioca starch), sodium starch glycollate, croscarmellose sodium and certain complex silicates, and granulation binders such as polyvinylpyrrolidone, hydroxypropyl-methylcellulose (HPMC), hydroxypropylcellulose (HPC), sucrose, gelatin and acacia. Additionally, lubricating agents such as magnesium stearate, stearic acid, glyceryl behenate and talc may be included.

Solid compositions of a similar type may also be employed as fillers in gelatin capsules. Preferred excipients in this regard include lactose, starch, cellulose, milk sugar or high molecular weight polyethylene glycols. For aqueous suspensions and/or elixirs, the compound may be combined with various sweetening or flavouring agents, colouring matter or dyes, with emulsifying and/or suspending agents and with diluents such as water, ethanol, propylene glycol and glycerin, and combinations thereof.

The routes for administration (delivery) include, but are not limited to, one or more of: oral (e.g. as a tablet, capsule, or as an ingestable solution), topical, mucosal (e.g. as a nasal spray or aerosol for inhalation), nasal, parenteral (e.g. by an injectable form), gastrointestinal, intraspinal, intraperitoneal, intramuscular, intravenous, intrauterine, intraocular, intradermal, intracranial, intratracheal, intravaginal, intracerebroventricular, intracerebral, subcutaneous, ophthalmic (including intravitreal or intracameral), transdermal, rectal, buccal, vaginal, epidural, sublingual.

Where the composition comprises more than one compound, it is to be understood that hot all of the components of the pharmaceutical need be administered by the same route. Likewise, if the composition comprises more than one active component, then those components may be administered by different routes.

If a component of the present invention is administered parenterally, then examples of such administration include one or more of: intravenously, intra-arterially, intraperitoneally, intrathecally, intraventricularly, intraurethrally, intrasternally, intracranially, intramuscularly or subcutaneously administering the component; and/or by using infusion techniques.

For parenteral administration, the component is best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art.

As indicated, the component(s) of the present invention can be administered intranasally or by inhalation and is conveniently delivered in the form of a dry powder inhaler or an aerosol spray presentation from a pressurised container, pump, spray or nebuliser with the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A™) or 1,1,1,2,3,3,3-heptafluoropropane (HFA 227EA™), carbon dioxide or other suitable gas. In the case of a pressurised aerosol, the dosage unit may be determined by providing a valve to deliver a metered amount. The pressurised container, pump, spray or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of the agent and a suitable powder base such as lactose or starch.

Alternatively, the component(s) of the present invention can be administered in the form of a suppository or pessary, or it may be applied topically in the form of a gel, hydrogel, lotion, solution, cream, ointment or dusting powder. The component(s) of the present invention may also be dermally or transdermally administered, for example, by the use of a skin patch. They may also be administered by the pulmonary or rectal routes. They may also be administered by the ocular route. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the component(s) of the present invention can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, it can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

In a preferred embodiment of the invention, the pharmaceutical composition is administered orally.

Dose Levels

Typically, a physician will determine the actual dosage which will be most suitable for an individual subject. The specific dose level and frequency of dosage for any particular patient may be varied and will depend upon a variety of factors including the activity of the specific compound employed, the metabolic stability and length of action of that compound, the age, body weight, general health, sex, diet, mode and time of administration, rate of excretion, drug combination, the severity of the particular condition, and the individual undergoing therapy.

Depending upon the need, the agent may be administered at a dose of from 0.01 to 30 mg/kg body weight, such as from 0.1 to 10 mg/kg, more preferably from 0.1 to 1 mg/kg body weight.

Therapy

The agents identified by any such assay method may be used as therapeutic agents—i.e. in therapy applications.

As with the term "treatment", the term "therapy" includes curative effects, alleviation effects, and prophylactic effects.

The therapy may be on humans or animals.

Where the composition is to be administered mucosally through the gastrointestinal mucosa, it should be able to remain stable during transit though the gastrointestinal tract; for example, it should be resistant to proteolytic degradation, stable at acid pH and resistant to the detergent effects of bile.

Where appropriate, the pharmaceutical compositions can be administered by inhalation, in the form of a suppository or pessary, topically in the form of a lotion, solution, cream, ointment or dusting powder, by use of a skin patch, orally in the form of tablets containing excipients such as starch or lactose, or in capsules or ovules either alone or in admixture with excipients, or in the form of elixirs, solutions or suspensions containing flavouring or colouring agents, or they can be injected parenterally, for example intravenously, intramuscularly or subcutaneously. For parenteral administration, the compositions may be best used in the form of a sterile aqueous solution which may contain other substances, for example enough salts or monosaccharides to make the solution isotonic with blood. For buccal or sublingual administration the compositions may be administered in the form of tablets or lozenges which can be formulated in a conventional manner.

For some embodiments, one or more compounds may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

General Assay Techniques

Another aspect of the invention relates to the use of a compound as defined hereinabove in an assay for identifying further candidate compounds that influence the activity of one or more CDK enzymes.

Preferably, the assay is capable of identifying candidate compounds that are capable of inhibiting one or more CDK enzymes.

More preferably, the assay is a competitive binding assay.

Preferably, the candidate compound is generated by conventional SAR modification of a compound of the invention.

As used herein, the term "conventional SAR modification" refers to standard methods known in the art for varying a given compound by way of chemical derivatisation.

Thus, in one aspect, the identified compound may act as a model (for example, a template) for the development of other compounds. The compounds employed in such a test may be free in solution, affixed to a solid support, borne on a cell surface, or located intracellularly. The abolition of activity or the formation of binding complexes between the compound and the agent being tested may be measured.

The assay of the present invention may be a screen, whereby a number of agents are tested. In one aspect, the assay method of the present invention is a high through-put screen.

Techniques for drug screening may be based on the method described in Geysen, European Patent Application 84/03564, published on Sep. 13, 1984. In summary, large numbers of different small peptide test compounds are synthesized on a solid substrate, such as plastic pins or some other surface. The peptide test compounds are reacted with a suitable compound or fragment thereof and washed. Bound entities are then detected—such as by appropriately adapting methods well known in the art. A purified compound can also be coated directly onto plates for use in a drug screening techniques. Alternatively, non-neutralising antibodies can be used to capture the peptide and immobilise it on a solid support.

This invention also contemplates the use of competitive drug screening assays in which neutralising antibodies capable of binding a compound specifically compete with a test compound for binding to a compound.

Another technique for screening provides for high throughput screening (HTS) of agents having suitable binding affinity to the substances and is based upon the method described in detail in WO 84/03564.

It is expected that the assay methods of the present invention will be suitable for both small and large-scale screening of test compounds as well as in quantitative assays.

Synthesis

The initial reaction in the methodology adopted for the synthesis of the compounds of this invention involved trityl protection of (R)- and (S)-2-amino-butan-1-ol (1 and 2) using trityl chloride (Evans, P. A.; Holmes, A. B.; Russel, K.; *J. Chem. Soc. Perkin Trans. I,* 1994, (23), 3397-3409.), to afford the protected amines 3 and 4, respectively, which then underwent Swern oxidation to their corresponding aldehydes (Takayama, H.; Ichikawa, T.; Kuwajimi, T.; Kitajima, M.; Seki, H.; Aimi, N.; Nonato, M. G.; *J. Am. Chem Soc.,* 2000, 122 (36), 8635-8639.) (5 and 6). Introduction of the 3'-alkyl functionalities to the (R)- and (S)-aldehyde stereoisomers (5 and 6) for production of the 3'-methyl (7 and 8), -isopropyl (11 and 12) and -tert-butyl intermediates (13 and 14) was accomplished via chelation-controlled alkylation (Reetz, M. T.; Rolfing, K.; Griebenow, N.; *Tetrahedron Lett.,* 1994, 35 (13), 1969-1972.). This involved reaction with copper bromide/dimethyl sulfide complex in ether, together with the appropriate alkyllithium reagent (i.e. methyllithium, isopropyllithium and tert-butyllithium, respectively).

For the methyl-substituted intermediates, this afforded the N-protected 2'R/3'S- and 2'S/3'R-diasteriomers (7 and 8) in approximately 80% de, while for the isopropyl-(11 and 12) and tert-butyl-substituted intermediates (13 and 14), alkylation was non-stereospecific for both the 2'R and 2'S stereoisomers to give approximately a 1:1 mixture of 3'R:3'S. As ethyllithium was not commercially available, an alternative methodology was followed for introduction of the 3'-ethyl-substituent, involving treatment of the aminoaldehydes (5 and 6) with ethylmagnesium bromide in ether, which again resulted in non-stereospecific addition of the ethyl substituent at the 3'-position, to afford approximately a 1:1 mixture of 3'R:3'S for both diastereoisomers (9 and 10).

For production of the trityl-protected-3'-dimethyl amino alcohol intermediates (25 and 26), the 3'-methyl substituted diasteriomers (7 and 8) initially underwent Swern oxidation to their respective ketones (23 and 24), followed by introduction of the second 3'-methyl using methylmagnesium iodide in refluxing ether.

The final step in the synthesis for all the aminoalcohols involved removal of the trityl groups using TFA in DCM to afford their equivalent N-deprotected intermediates (15, 16, 17, 18, 19, 20, 21, 22, 27 and 28).

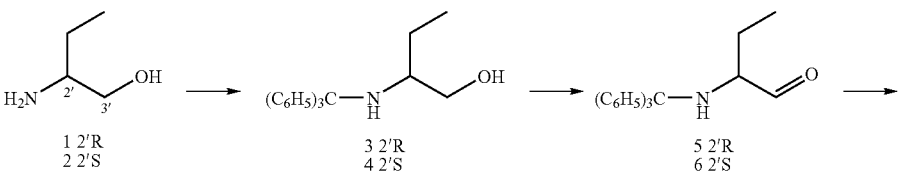

1 2'R
2 2'S 3 2'R
4 2'S 5 2'R
6 2'S

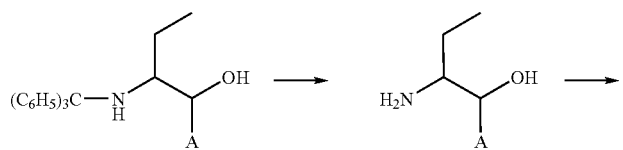

7 A = CH₃, 2'R/3'S
8 A = CH₃, 2'S/3'R

9 A = CH₂CH₃, 2'R/3'RS
10 A = CH₂CH₃, 2'S/3'RS

11 A = CH(CH₃)₂, 2'R/3'RS
12 A = CH(CH₃)₂, 2'S/3'RS

13 A = ᵗBu, 2'R/3'RS
14 A = ᵗBu, 2'S/3'RS

15 A = CH₃, 2'R/3'S
16 A = CH₃, 2'S/3'R

17 A = CH₂CH₃, 2'R/3'RS
18 A = CH₂CH₃, 2'S/3'RS

19 A = CH(CH₃)₂, 2'R/3'RS
20 A = CH(CH₃)₂, 2'S/3'RS

21 A = ᵗBu, 2'R/3'RS
22 A = ᵗBu, 2'S/3'RS

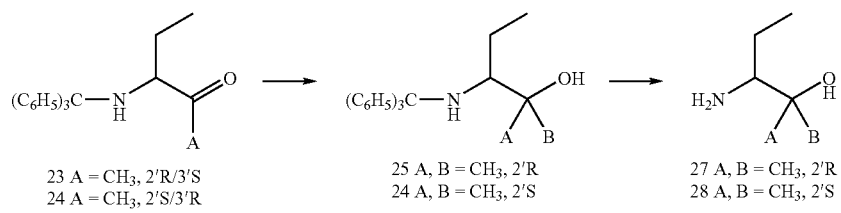

23 A = CH₃, 2'R/3'S
24 A = CH₃, 2'S/3'R

25 A, B = CH₃, 2'R
24 A, B = CH₃, 2'S

27 A, B = CH₃, 2'R
28 A, B = CH₃, 2'S

For the synthesis of the 6-benzylamino-, 6-(pyridin-2-yl-methyl), 6-(pyridin-3-ylmethyl) and 6-(pyridin-2-ylmethyl)-intermediates, the initial step involved reaction of 6-chloro-2-fluoro-purine 29 [Gray, N. S.; Kwon, S.; Schultz, P. G. *Tetrahedron Lett.*, 1997, 38 (7), 1161-1164] with either benzylamine, 2-(aminomethyl)pyridine, 3-(aminomethyl)pyridine or 4-(aminomethyl)pyridine, in n-BuOH the presence of DIPEA, to afford the corresponding 6-substituted intermediates 30. These compounds then underwent reaction with 2-bromopropane and $K_2CO_3$ in DMA [Havlicek, L.; Hunus, J.; Vesely, J.; Leclerc, S.; Meijer; L.; Shaw, G.; Strnad, M.; *J Med Chem.*, 1997, 40 (4), 408412], to afford their corresponding N9-isopropyl substituted intermediates 31. These purine intermediates were finally reacted with the aminoalcohols (1-2, 15-22, and 27-28) in DMSO/n-BuOH/DIEA at 140° C. over 72 h to give their corresponding $C_2$-substituted aminoalkyl analogues 32.

The present invention will now be described by way of example.

EXAMPLES

The following abbreviations are used throughout the experimental section:

| | |
|---|---|
| DE-MALDI-TOF MS | Delayed extraction matrix-assisted laser desorption ionization time-of-flight mass spectrometry |
| DBU | 1,8-diazabicyclo[5.4.0]undec-7-ene |
| DMA | Dimethylacetamide |
| DMSO | Dimethylsulfoxide |
| FAB-MS | Fast atom bombardment mass spectrometry |
| NMP | 1-methyl-2-pyrrolidinone |
| NMR | Nuclear magnetic resonance spectroscopy |
| RP-HPLC | Reversed-phase high-performance liquid chromatography |
| RT | RT |
| TLC | Thin-layer chromatography |
| DCM | Dichloromethane |
| de | Diastereomeric excess |
| DIBA | Diisopropylethylamine |

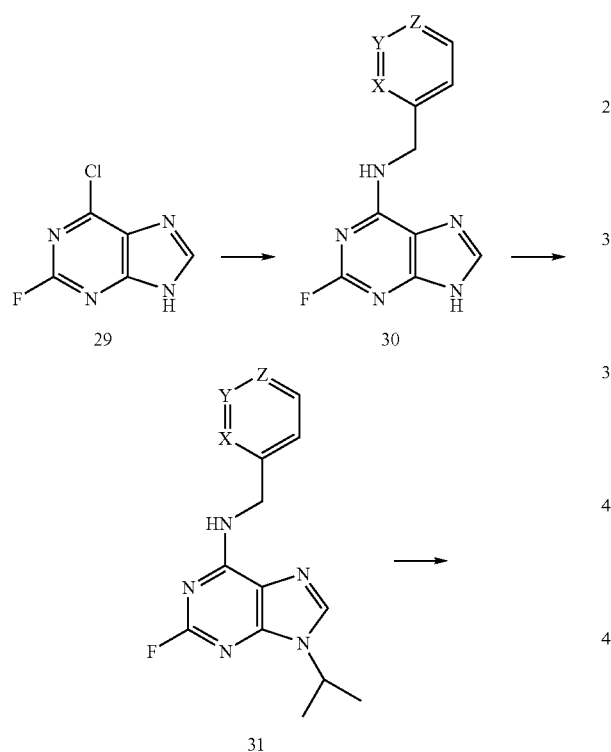

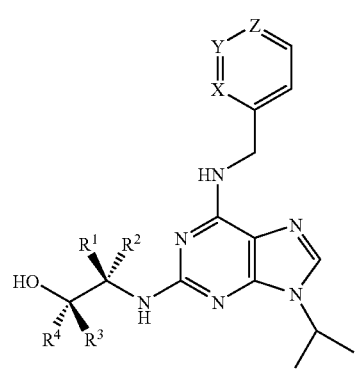

Example 1

1-[9-Cyclopentyl-6-(indan-5-ylamino)-9H-purin-2-yl]-piperidin-3-ol

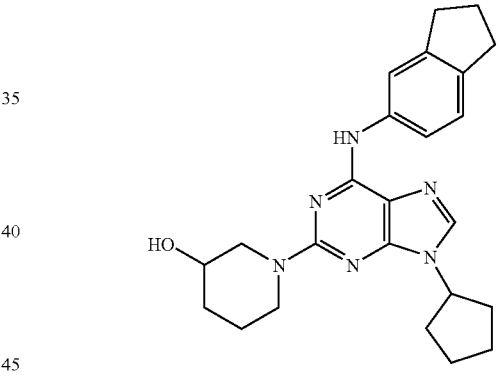

(2-Chloro-9H-purin-6-yl)-indan-5-yl-amine 2,6-Dichloro-9H-purine (1.89 g, 10 mmol), 5-aminoindan (1.33 g, 10 mmol) and $Et_3N$ (2.79 mL, 20 mmol) were dissolved in Bu''OH (15 mL). The solution was stirred for 2 h at 90° C. After cooling, Pr'OH (90 mL) was added slowly with stirring. After 1 h the precipitate was filtered, washed successively with small quantities of Pr'OH and $Pr^j_2O$, and dried in vacuo to afford the title compound as a lemon-coloured powder (1.54 g, 54.1%). TLC (80:15:5 $CHCl_3$/MeOH/AcOH): $R_F$=0.61.

(2-Chloro-9-cylopentyl-9H-purin-6-yl)-indan-5-yl-amine (2-Chloro-9H-purin-6-yl)-indan-5-yl-amine (857 mg, 3 mmol) was dissolved in dry DMF (10 mL). NaH (94 mg, 3.9 mmol) was added in portions and the resulting mixture was stirred for 1 h. Cyclopentyl bromide (760 mg, 5.1 mmol) was then added and the reaction was stirred overnight at 80° C.

under N₂. After cooling, H₂O (50 mL) was added and the mixture was extracted with CH₂Cl₂ (3×25 mL). The combined extracts were washed with brine (2×25 mL), dried over MgSO₄, and evaporated. The residue was purified by flash chromatography (95:5 CH₂Cl₂/Et₂O) to afford the title compound as a white powder (738 mg, 69.5%). TLC (95:5 CH₂Cl₂/Et₂O): $R_F$=0.38.

1-[9-Cyclopentyl-6-(indan-5-ylamino)-9H-purin-2-yl]-piperidin-3-ol (2-Chloro-9-cyclopentyl-9H-purin-6-yl)-indan-5-yl-amine (283 mg, 0.8 mmol), 3-hydroxypiperidine hydrochloride (550 mg, 4 mmol) and K₂CO₃ (829 mg, 6 mmol) were suspended in 2,5-lutidine (10 mL) and the mixture was heated at 180° C. for 4 h. After cooling, CH₂Cl₂ (50 mL) was added and the solution was extracted with brine (2×15 mL). The organic fraction was dried over MgSO₄, filtered and evaporated. The residue was purified by flash chromatography (95:5 CH₂Cl₂/MeOH) to afford the title compound as a slightly yellow foam (320 mg, 95.6%). Anal. RP-HPLC (Phenomenex Jupiter, 5 μ, C18, 300 Å, 4.6×250 mm; 1 mL/min): $t_R$=19.6 min (10-70% MeCN in 0.1% aq CF₃COOH over 20 min); $t_R$=15.4 min (40-50% MeCN in 0.1% aq CF₃COOH over 20 min); purity>92% (λ=214 nm). DE-MALDI-TOF MS: [M+H]⁺=419.5 (C₂₄H₃₀N₆O=418.5).

Example 2

1-[9-Cyclopentyl-6-(3,4-dimethoxy-benzylamino)-9H-purin-2-yl]piperidin-3-ol

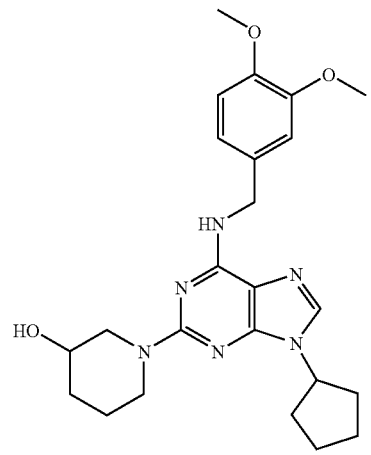

(2-Chloro-9H-purin-6-yl)-(3,4-dimethoxy-benzyl)-amine 2,6-Dichloro-9H-purine (1.7 g, 9 mmol), veratrylamine (1.5 g, 9 mmol) and Et₃N (2.51 mL, 18 mmol) were dissolved in Bu"OH (10 ML). The solution was stirred for 2 h at 90° C. After cooling, Pr$^i$OH (90 mL) was added slowly with stirring. After 1 h the precipitate was filtered, washed successively with small quantities of Pr$^i$OH and Pr$^i_2$O, and dried in vacuo to afford the title compound as a white powder (2.69 g, 93.4%). TLC (9:1 CH₂Cl₃/MeOH/AcOH): $R_F$=0.33.

(2-Chloro-9-cyclopentyl-9H-purin-6-yl)-(3,4-dimethoxy-benzyl)-amine (2-Chloro-9H-purin-6-yl)-(3,4-dimethoxy-benzyl)-amine (799 mg, 2.5 mmol) was dissolved in dry DMF (10 mL). NaH (78 mg, 3.25 mmol) was added in portions and the resulting mixture was stirred for 1 h. Cyclopentyl bromide (633 mg, 4.25 mmol) was then added and the reaction was stirred overnight at 80° C. under N₂. After cooling, H₂O (50 mL) was added and the mixture was extracted with CH₂Cl₂ (3×25 mL). The combined extracts were washed with brine (2×25 mL), dried over MgSO₄, and evaporated. The residue was purified by flash chromatography (95:5 CH₂Cl₂/Et₂O) to afford the title compound as a white powder (451 mg, 46.5%). TLC (95:5 CH₂Cl₂/Et₂O): $R_F$=0.27.

1-[9-Cyclopentyl-6-(3,4-dimethoxy-benzylamino)-9H-purin-2-yl]-piperidin-3-ol (2-Chloro-9-cyclopentyl-9H-purin-6-yl)-(3,4-dimethoxy-benzyl)-amine (446 mg, 1.15 mmol), 3-hydroxypiperidine hydrochloride (791 mg, 5.75 mmol) and K₂CO₃ (1.19 mg, 8.63 mmol) were suspended in 2,5-lutidine (10 mL) and the mixture was heated at 180° C. for 4 h. After cooling, CH₂Cl₂ (50 mL) was added and the solution was extracted with brine (2×15 mL). The organic fraction was dried over MgSO₄, filtered and evaporated. The residue was purified by flash chromatography (95:5 CH₂Cl₂/MeOH) to afford the title compound as an off-white foam (427 mg, %). Anal. RP-HPLC (Phenomenex Jupiter, 5 μ, C18, 300 Å, 4.6×250 mm; 1 mL/min): $t_R$=18.4 min (10-70% MeCN in 0.1% aq CF₃COOH over 20 min); $t_R$=16.0 min (35-45% MeCN in 0.1% aq CF₃COOH over 20 min); purity>95% (λ=214 nm). DE-MALDI-TOF MS: [M+H]⁺=453.9 (C₂₄H₃₂N₆O₃=452.6).

Example 3

(R)-2-[9-Isopropyl-6-(3-nitro-phenylamino)-9H-purin-2-ylamino]-3-methyl-butan-1-ol

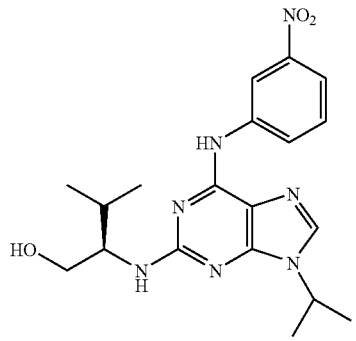

(2-Chloro-9H-purin-6-yl)-(3-nitro-phenyl)-amine 2,6-Dichloro-9H-purine (650 mg, 3.44 mmol) and 3-nitroaniline (1.9 g, 13.76 mmol) were stirred in 1-pentanol (5 mL) at 100° C. for 2 h under N₂. The mixture was cooled and diluted with Et₂O (40 mL). The precipitate was filtered and washed successively on a sinter with Et₂O, Pr$^i$OH, H₂O, 10% aq Na₂CO₃, H₂O, Pr$^i$OH, and Et₂O (2×20 mL each). It was then dried in vacuo to afford the title compound as a lemon-yellow powder (1.01 g, quant.). TLC (9:1 CH₂Cl₂/MeOH): $R_F$=0.35.

(2-Chloro-9-isopropyl-9H-purin-6-yl)-(3-nitro-phenyl)-amine (2-Chloro-9H-purin-6-yl)-(3-nitro-phenyl)-amine (872 mg, 3 mmol) was dissolved in dry DMF (10 mL). NaH (122 mg, 5.1 mmol) was added in portions and the resulting mixture was stirred for 1 h. 2-Bromopropane (480 mg, 3.9 mmol) was then added and the reaction was stirred overnight at 80° C. under $N_2$. After cooling, $H_2O$ (50 mL) was added slowly with stirring and cooling. After 1 h, precipitated product was filtered, washed with more cold $H_2O$, and dried in vacuo to afford the title compound as a lemon-yellow powder (905 mg, 90.7%). TLC (95:5 $CH_2Cl_2$/MeOH): $R_F$=0.46.

2-[9-Isopropyl-6-(3-nitro-phenylamino)-9H-purin-2-ylamino]-3-methyl-butan-1-ol (2-Chloro-9-isopropyl-9H-purin-6-yl)-(3-nitro-phenyl)-amine (333 mg, 1 mmol), D-valinol (310 mg, 3.0 mmol), and DBU (457 mg, 3.0 mmol) were stirred in NMP (5 mL) overnight at 150° C. under $N_2$. After cooling, the mixture was diluted with $H_2O$ (40 mL) and was extracted with $CH_2Cl_2$ (3×25 mL). The combined extracts were washed with brine, treated with decolourising charcoal and $MgSO_4$, filtered, and evaporated. The residue was redissolved in DMSO/$H_2O$ and chromatographed (Vydac 218TP1022; 9 mL/min, 27.5-37.5% MeCN in 0.1% aq $CF_3COOH$ over 40 min). Appropriate peak fractions were pooled and lyophilized to afford the title compound as an orange solid (12.3 mg). Anal. RP-HPLC (Vydac 218TP54; 1 mL/min): $t_R$=15.8 min (27.5-37.5% MeCN in 0.1% aq $CF_3COOH$ over 20 min); purity>95% ($\lambda$=214 nm). DE-MALDI-TOF MS: [M+H]$^+$=398.5 ($C_{19}H_{25}N_7O_3$=399.5).

Example 4

(R)-2-[9-Isopropyl-6-(3-nitro-phenlamino)-9H-purin-2-ylamino]-butan-1-ol

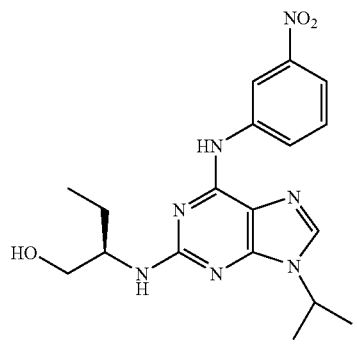

A mixture of (2-chloro-9-isopropyl-9H-purin-6-yl)-(3-nitro-phenyl)-amine (333 mg, 1 mmol) and (R)-(−)-2-amino-1-butanol (1.78 g, 20 mmol) was stirred at 160° C. for 3 h under $N_2$. After cooling, $CHCl_3$ (50 mL) was added and the solution was extracted with brine (2×25 mL). The organic fraction was dried over $MgSO_4$, filtered, and evaporated. The residue was purified by flash chromatography (95:5 $CH_2Cl_2$/MeOH) to afford the title compound as a yellow glassy solid (104 mg, 27.0%). Anal. RP-HPLC (Vydac 218TP54; 1 mL/min): $t_R$=16.8 min (0-60% MeCN in 0.1% aq $CF_3COOH$ over 20 min); purity>95% ($\lambda$=214 nm). DE-MALDI-TOF MS: [M+H]$^+$=384.7 ($C_{18}H_{23}N_7O_3$=385.4).

Example 5

(R)-2-{9-Isopropyl-6-[(pyridin-2:ylmethyl)-amino]-9H-purin-2:ylamino}-butan-1-ol

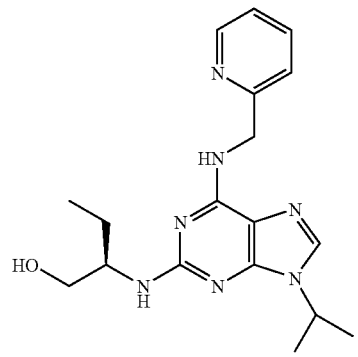

(2-Fluoro-9H-purin-6-yl)-pyridin-2-ylmethyl-amine

To a stirred solution of 6-chloro-2-fluoro-9H-purine (prepared according to Gray, N. S.; Kwon, S.; Schultz, P. G. *Tetrahedron Lett* 1997, 38, 1161-1164; 0.4 g, 2.31 mmol) in Bu$^n$OH (25 mL) under Ar, cooled to 0° C., was added Pr$^i_2$NEt (1.13 mL, 6.49 mmol) followed by 2-(aminomethyl)pyridine (0.48 mL, 4.66 mmol). The reaction mixture was stirred at 0° C. for 3 h, and then allowed to return to RT over 30 min. and stirred at this temperature for 1 h, when TLC (9:1 $CHCl_3$/MeOH) indicated that the reaction had gone to completion. The solvent was evaporated in vacuo and the residue partitioned between citric acid solution (200 mL, 10% aq) and EtOAc (200 mL), the aqueous phase was separated and extracted with more EtOAc (2×100 mL). The pH of the aqueous phase was adjusted to 7.0 with NaOH solution (50% w/v, aq), extracted with EtOAc (4×100 mL), and the bulked organic phase was washed with brine (50 mL), dried ($MgSO_4$) and evaporated in vacuo. The residue was purified by gradient column chromatography on silica gel, eluted with $CHCl_3$/MeOH (95:5→85:15), to afford the title compound as a light yellow solid (0.40 g, 71%). Mp 217-220° C. $^1$H-NMR (d$_6$-DMSO, 250 MHz): δ 4.58 (d, 2H, J=5.68 Hz, —HN CH$_2$-Pyr), 7.29, 7.71, 8.49 (3×m, 4H, Pyr), 8.10 (s, 1H, —N=CH—NH—), 8.69 (bs, 1H, —HNCH$_2$-Pyr), 13.07 (bs, 1H, —N=CH—NH—). FAB-MS m/z (relative intensity): 245 ([M+H]$^+$, 55), 176 (30), 154 (100), 136 (85). Accurate Mass (M+H): Actual: 245.0951, Measured: 245.0942. Microanalysis (Expected:Measured) $C_{11}H_9N_6F$.0.4$H_2O$: C, 52.55:52.91; H, 3.93:3.49; N, 33.42:33.26.

(2-Fluoro-9-isopropyl-9H-purin-6-yl)-pyridin-2-yl-amine

To a stirred solution of (2-fluoro-9H-purin-6-yl)-pyridin-2-ylmethyl-amine (0.4 g, 1.64 mmol) in DMA (5 mL) under Ar, at RT, was added $K_2CO_3$ (powdered, anhydrous; 1.1 g, 7.96 mmol) followed 2-bromopropane (1.5 mL, 15.98 mmol). The reaction mixture was stirred at 40° C. for 48 h, when TLC (9:1 $CHCl_3$/MeOH) indicated that the reaction had gone to completion. The solvent was evaporated in vacuo and the residue partitioned between $H_2O$ (200 mL) and EtOAc (100 mL), the aqueous phase was separated and extracted with more EtOAc (2×50 mL). The bulked organic phase was washed with brine (50 mL), dried (MgSO$_4$) and evaporated in vacuo, and the residue was purified by gradient column chromatography on silica gel, eluted with CHCl$_3$/MeOH (100:0→95:5), to afford the title compound as a white solid (0.27 g, 58%). Mp 150-152° C. $^1$H-NMR (d$_6$-DMSO, 250 MHz): δ 1.49 (2×s, 6H, CH(CH$_3$)$_2$), 4.63 (m, 1H, —CH(CH$_3$)$_2$), 4.71 (d, 2H, J=5.76 Hz, —HNCH$_2$-Pyr), 7.26, 7.71, 8.49 (3×m, 4H, Pyr), 8.26 (s, 1H, —N═CH—N—), 8.78 (bs, 1H, —HNCH$_2$-Pyr). FAB-MS m/z (relative intensity): 287 ([M+H]$^+$, 100), 245 (10), 154 (22), 136 (17). Accurate Mass (M+H): Actual: 287.1420, Measured: 287.1412. Microanalysis (Expected:Measured) C$_{14}$H$_{15}$N$_6$F: C, 58.73:58.38; H, 5.28:5.13; N, 29.35:29.36.

(R)-2-[9-Isopropyl-6-(pyridin-2-ylamino)-9H-purin-2-ylamino]-butan-1-ol

To a stirred solution of (2-fluoro-9-isopropyl-9H-purin-6-yl)-pyridin-2-yl-amine (0.25 g, 0.87 mmol) in Bu$^n$OH/DMSO (5 mL, 4:1) at RT under Ar was added Pr$^i_2$NEt (1.5 mL, 8.61 mmol) followed by. (R)-(−)-2-aminobutan-1-ol (0.82 mL, 8.71 mmol). The reaction mixture was placed in a preheated oil bath at 140° C. and stirred at this temperature for 72 h, when TLC (9:1 CHCl$_3$/MeOH) indicated that the reaction had gone to completion. The reaction mixture was allowed to cool to RT and the solvent was evaporated in vacuo. The residue was partitioned between EtOAc (100 mL) and H$_2$O (150 mL), the aqueous, phase was extracted with more EtOAc (2×50 mL), and the combined organic phase was washed with brine (50 mL), dried (MgSO$_4$) and evaporated in vacuo. The residue was purified by gradient column chromatography on silica gel eluted with CHCl$_3$/MeOH (100:0→97:3), to afford the title compound as a white solid (0.29 g, 95%). Mp 30-35° C. $^1$H-NMR (d$_6$-DMSO, 250 MHz): δ 0.77 (m, 3H, —NHCH(CH$_2$CH$_3$)CH$_2$OH), 1.24-1.48 (m, 8H, —NHCH(CH$_2$CH$_3$)CH$_2$OH+CH(CH$_3$)$_2$), 3.38 (m, 2H, —NHCH(CH$_2$CH$_3$)CH$_2$OH), 3.70 (m, 1H, —NHCH(CH$_2$CH$_3$)CH$_2$OH), 4.52 (m, 2H, —NHCH$_2$-Pyr), 4.75 (m, 2H, OH+CH(CH$_3$)$_2$), 5.81 (d, 2H, J=8.33 Hz, —NHCH(CH$_2$CH$_3$)CH$_2$OH), 7.24, 7.67, 8.48 (3×m, 4H, Pyr), 7.79 (bs, 2H, —N═CH—N+—HNCH$_2$-Pyr). FAB-MS m'z (relative intensity): 356 ([M+H]$^+$, 100), 324 (28), 154 (26), 136 (22). Accurate Mass (M+H: Actual: 356.2199, Measured: 356.2208. Microanalysis (Expected:Measured) C$_{18}$H$_{25}$N$_7$O: C, 60.83:61.81; H, 7.09:7.29; N, 27.58:27.09.

Example 6

(R)-2-{9-Isopropyl-6-[(pyridin-4-ylmethyl)-amino]-9H-purin-2-ylamino}-butan-1-ol

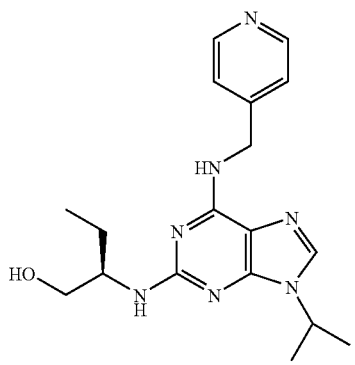

(2-Fluoro-9H-purin-6-yl)-pyridin-4-ylmethyl-amine

To a stirred solution of 6-chloro-2-fluoro-9H-purine (0.9 g, 5.22 mmol) in Bu$^n$OH (60 mL) under Ar, cooled to −20° C., was added Pr$^i_2$NEt (2.5 mL, 14.35 mmol) followed by 4-(aminomethyl)pyridine (0.58 mL, 5.69 mmol). The reaction mixture was stirred at-20° C. for 3 h, and then allowed to return to RT over 2 h and stirred at RT for a further 48 h, when TLC (9:1 CHCl$_3$/MeOH) indicated that the reaction had gone to completion. The solvent was evaporated in vacuo and the residue was purified by gradient column chromatography on silica gel, eluted with CHCl$_3$/MeOH (100:0→90:10), to afford the title compound as a white solid (0.69 g, 54%). Mp>340° C. $^1$H-NMR (d$_6$-DMSO, 250 ME): δ 4.67 (d, 2H, J=6.35 Hz, —HNCH$_2$-Pyr), 7.34, 8.50 (2×m, 4H, Pyr), 8.14 (s, 1H, —N═CH—NH—), 8.84 (bs, 1H, —HNCH$_2$-Pyr), 13.13 (bs, 1H, —N═CH—NH—). FAB-MS m/z (relative intensity): 245 ([M+H]$^+$, 27), 176 (15), 154 (100), 136 (77). Accurate Mass (M+H): Actual: 245.0951, Measured: 245.0942. Microanalysis (Expected:Measured) C$_{11}$H$_9$N$_6$F.0.6H$_2$O: C, 51.80:52.08; H, 4.03:3.84; N, 32.95:31.29.

(2-Fluoro-9-isopropyl-9H-purin-6-yl)-pyridin-4-yl-amine

To a stirred solution of (2-fluoro-9H-purin-6-yl)-pyridin-4-ylmethyl-amine (0.6 g, 2.46 mmol) in DMA (10 mL) under Ar, at RT, was added K$_2$CO$_3$ (powdered, anhydrous, 1.65 g, 11.93 mmol) followed by 2-bromopropane (2.25 mL, 23.96 mmol). The reaction mixture was stirred at RT for 48 h, when TLC (9:1 CHCl$_3$/MeOH) indicated that the reaction had gone to completion. The solvent was evaporated in vacuo and the residue partitioned between H$_2$O (200 mL) and EtOAc (100 mL), the aqueous phase was separated and extracted with more EtOAc (2×50 mL). The bulked organic phase was washed with brine (50 mL), dried (MgSO$_4$) and evaporated in vacuo, and the residue was purified by gradient column chromatography on silica gel, eluted with CHCl$_3$/MeOH (100:0→95:5), to afford the title compound as a white solid (0.40 g, 57%). Mp 270-273° C. $^1$H-NMR (d$_6$-DMSO, 250 MHz): δ 1.49 (2×s, 6H, —CH(CH$_3$)$_2$), 4.63 (m, 3H, —CH(CH$_3$)$_2$+—HNCH$_2$-Pyr) 7.30, 8.47 (2×m, 4H, Pyr), 8.28 (s, 1H, —N═CH—N—), 8.97 (bs, 1H, —HNCH$_2$-Pyr). FAB-MS m/z (relative intensity): 287 ([M+H)]$^+$, 100), 245 (8), 154 (23), 136 (18). Accurate Mass (M+H): Actual: 287.1420, Measured: 287.1412. Microanalysis (Expected:Measured) C$_{14}$H$_{15}$N$_6$F: C, 58.73:58.57; H, 5.28:5.21; N, 29.35:29.27.

(R)-2-[9-Isopropyl-6-pyridin-4-ylamino)-9H-purin-2-ylamino]-butan-1-ol

To a stirred solution of (2-fluoro-9-isopropyl-9H-purin-6-yl)-pyridinyl-amine (0.27 g, 0.94 mmol) in Bu$^n$OH/DMSO (5 mL, 4:1) at RT under Ar was added Pr$^i_2$NEt (1.63 nm, 9.36 mmol) followed by (R)-(−)-2-aminobutan-1-ol (0.89 mL, 9.45 mmol). The reaction mixture was placed in a preheated oil bath at 140° C. and stirred at this temperature for 48 h, when TLC (9:1 CHCl$_3$/MeOH) indicated that the reaction had gone to completion The reaction mixture was allowed to cool to RT and the solvent was evaporated in vacuo. The residue was partitioned between EtOAc (100 mL) and H$_2$O (150 mL), the aqueous phase was saturated with NaCl and extracted with more EtOAc (2×50 mL), and the combined organic phase was washed with brine (50 mL), dried MgSO$_4$)

and evaporated in vacuo. The residue was purified by gradient column chromatography on silica gel eluted with CHCl$_3$/MeOH (100:0→97:3), to afford the title compound as a white solid (0.30 g, 89%). Mp 105-106° C. $^1$H-NMR (d$_6$-DMSO, 250 MHz): δ 0.78 (m, 3H, —NHCH(CH$_2$CH$_3$)CH$_2$OH), 1.39-1.55 (m, 8H, —NHCH(CH$_2$CH$_3$)CH$_2$OH+—CH(CH$_3$)$_2$), 3.32, 3.40 (2×m, 2H, —NHCH(CH$_2$CH$_3$) CH$_2$OH), 3.70 (m, 1H, —NHCH(CH$_2$CH$_3$)CH$_2$OH), 4.50-4.64 (m, 4H, —HN CH$_2$-Pyr+CH(CH$_3$)$_2$+OH), 5.83 (d, 2H, J=8.15 Hz, —N HCH(CH$_2$CH$_3$)CH$_2$OH), 7.30, 8.45 (2×m, 4H, Pyr), 7.80 (s, 1H, —N=CH—N—), 7.88 (bs, 1H, —HNCH$_2$-Pyr). FAB-MS m/z (relative intensity): 356 ([M+H]$^+$, 100), 324 (28), 154 (47), 136 (38). Accurate Mass (M+H): Actual: 356.2199, Measured: 356.2208. Microanalysis (Expected:Measured) C$_{18}$H$_{25}$N$_7$O: C, 60.83:60.99; H, 7.09:7.25; N, 27.58: 26.94.

Example 7

3-(6-Benzylamino-9-isopropyl-9H-purin-2-ylamino-pentan-2-ol

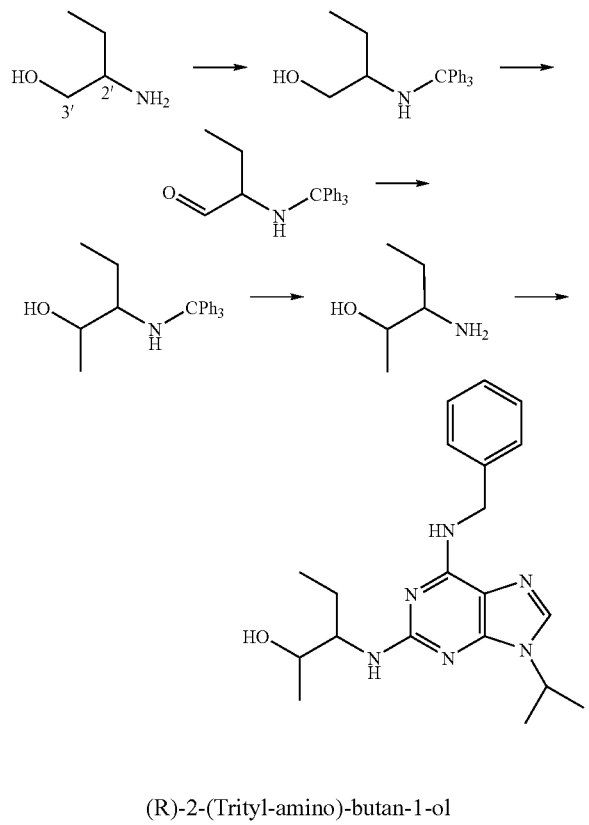

(R)-2-(Trityl-amino)-butan-1-ol

To a stirred solution of (R)-(−)-2-aminobutan-1-ol (10 g, 112.18 mmol) in CH$_2$Cl$_2$ (500 mL) under Ar at RT, was added Pr$^i$$_2$NEt (30 mL, 172.22 mmol) followed by trityl chloride (35.4 mL, 126.98 mmol). The reaction mixture was stirred at RT for 48 h, when TLC (55:40:5 hexane/Et$_2$O/MeOH) indicated that the reaction had gone to completion. The solvent was evaporated in vacuo and the residue precipitated from Me$_2$CO (50 mL) with hexane (900 mL) with stirring, the precipitate was removed by filtration and the filtrate was evaporated in vacuo. The residue was dissolved in hexane (1 L), filtered, and the filtrate was evaporated in vacuo to afford the title compound as a light yellow oil (32 g, 86%). $^1$H-NMR (d$_6$-DMSO, 250 MHz): δ 0.56 (t, 3H, J=7.41, —NHCH(CH$_2$CH$_3$)CH$_2$OH), 1.10 (m, 2H, —NHCH(CH$_2$CH$_3$)CH$_2$OH), 2.21 (m, 1H, —NHCH(CH$_2$CH$_3$)CH$_2$OH), 2.72+3.00 (2×m, 2H, —NHCH(CH$_2$CH$_3$)CH$_2$OH), 4.28 (t, 1H, J=5.26 Hz, —NHCH(CH$_2$CH$_3$)CH$_2$OH), 7.14-7.49 (m, 15H, 3×Bz).

(S)-2-(Trityl-amino)-butan-1-ol

To a stirred solution of (S)-(+)-2-aminobutan-1-ol (10 g, 112.18 mmol) in CH$_2$Cl$_2$ (500 mL) under Ar at RT, was added Pr$^i$$_2$NEt (30 mL, 172.22 mmol) followed by trityl chloride (35.4 mL, 126.98 mmol). The reaction mixture was stirred at this temperature for 48 h, when TLC (55:40:5 hexane/Et$_2$O/MeOH) indicated that the reaction had gone to completion. The solvent was evaporated in vacuo and the residue precipitated from Me$_2$CO (50 mL) with hexane (900 mL) with stirring, the precipitate was removed by filtration and the filtrate was evaporated in vacuo. The residue was dissolved in hexane (1 L), filtered, and the filtrate was evaporated in vacuo to afford the title compound as a light yellow oil (33 g, 89%). $^1$H-NMR (d$_6$-DMSO, 250 MHz): δ 0.58 (t, 3H, J=7.26, —NHCH(CH$_2$CH$_3$)CH$_2$OH), 1.10 (m, 2H, —NHCH(CH$_2$CH$_3$)CH$_2$OH), 2.24 (m, 1H, —NHCH(CH$_2$CH$_3$)CH$_2$OH), 2.76+3.03 (2×m, 2H, —NHCH(CH$_2$CH$_3$)CH$_2$OH), 4.32 (t, 1H, J=4.97 Hz, —NHCH(CH$_2$CH$_3$)CH$_2$OH), 7.15-7.52 (m, 15H, 3×Bz).

(R)-2-(Trityl-amino)-butyraldehyde

To a stirred solution of DMSO (3.0 mL, 42.28 mmol) in CH$_2$Cl$_2$ (30 mL) under Ar at −45° C., was added oxalyl chloride (2 M in CH$_2$Cl$_2$, 10.56 mL, 21.12 mmol) dropwise. The reaction mixture was stirred at −45° C. for 1 h, after which time a solution of (R)-2-(trityl-amino)-butan-1-ol (5 g, 15.08 mmol) in CH$_2$Cl$_2$ (30 mL) was added dropwise with stirring. The reaction mixture was sired at this temperature for 3 h, when TLC (8:2 hexane/Et$_2$O) indicated that the reaction had gone to completion. Et$_3$N (10.5 mL, 75.33 mmol) in CH$_2$Cl$_2$ (30 mL) was added and the solution was allowed to warm to RT over 16 h. It was diluted with more CH$_2$Cl$_2$ (200 mL) and washed with H$_2$O (250 mL). The aqueous phase was extracted with CH$_2$Cl$_2$ (3×50 mL) and the combined organic phases washed with brine (50 mL), dried (MgSO$_4$), and evaporated in vacuo. The residue was dissolved in Et$_2$O (30 mL), the solid precipitate was removed by filtration, and the filtrate was evaporated in vacuo. The residue was dissolved in hexane (50 mL), the solid precipitate was removed by filtration, and the filtrate was evaporated in vacuo to afford the title compound as a light yellow oil (2.59 g, 52%). $^1$H-NMR (d$_6$-DMSO, 250 MHz): δ 0.77 (t, 3H, J=7.42 Hz, —NHCH(CH$_2$CH$_3$)CHO), 1.34-1.61 (m, 2H, —NHCH(CH$_2$CH$_3$)CHO), 2.92 (m, 1H, —NHCH(CH$_2$CH$_3$)CHO), 3.62 (d, 1H, J=8.21 Hz, —NHCH(CH$_2$CH$_3$)CHO), 7.16-7.46 (m, 15H, 3×Bz), 8.77 (d, 1H, J=3.00 Hz, —NHCH(CH$_2$CH$_3$)CHO).

(S)-2-(Trityl-amino)-butyraldehyde

To a stirred solution of DMSO (2.4 mL, 33.82 mmol) in CH$_2$Cl$_2$ (30 mL) under an argon atmosphere at −45° C., was added oxalyl chloride (2M in CH$_2$Cl$_2$, 8.45 mL, 16.9 mmol) dropwise. The reaction mixture was stirred at −45° C. for 1 h, after which time a solution of (S)-2-(trityl-amino)-butan-1-ol (4 g, 12.07 mmol) in CH$_2$Cl$_2$ (30 mL) was added dropwise with stirring. Stirring was continued at this temperature for 3 h, when TLC (8:2 hexane/Et$_2$O) indicated that the reaction had gone to completion. Et$_3$N (8.4 mL, 60.27 mmol) in CH$_2$Cl$_2$ (30 mL) was added and the solution was allowed to warm to RT over 16 h. It was diluted with more CH$_2$Cl$_2$ (100 mL) and was washed with H$_2$O. (250 ml). The aqueous phase was extracted with CH$_2$Cl$_2$ (3×50 mL.) and the combined organic phases were washed with brine (50 mL), dried (MgSO$_4$), and evaporated in vacuo. The residue was dissolved in Et$_2$O (30 mL), the solid precipitate was removed by filtration, and the filtrate was evaporated in vacuo. The residue was dissolved in hexane (50 mL), the solid precipitate was removed by filtration, and the filtrate was evaporated in vacuo to afford the title compound as a light yellow oil (3.64 g, 91%). $^1$H-NMR (d$_6$-DMSO, 250 M): δ 0.77 (t, 3H, J=7.42 Hz, —NHCH(CH$_2$CH$_3$)CHO), 1.37-1.59 (m, 2H, —NHCH(CH$_2$CH$_3$)CHO), 2.93 (m, 1H, —NHCH(CH$_2$CH$_3$)CHO), 3.62 (d, 1H, J=5.84 Hz, —NHCH(CH$_2$CH$_3$)CHO), 7.16-7.46 (m, 15H, 3×Bz), 8.77 (d, 1H, J=3.00 Hz, —NHCH(CH$_2$CH$_3$)CHO).

(2S, 3R)-3-(Trityl-amino)-pentan-2-ol

To a stirred suspension of CuBr.SMe$_2$ (2.74 g, 13.33 mmol) in Et$_2$O (100 mL) under Ar e at −70° C., was added methyl lithium (1.6 M in Et$_2$O; 16.6 mL, 26.56 mmol) dropwise and the solution allowed to warm to RT. The mixture was re-cooled to −70° C., to which was added a solution of (R)-2-(trityl-amino)-butyraldehyde (2 g, 6.05 mmol) in. Et$_2$O (25 mL) dropwise with stirring. The reaction mixture was stirred at this temperature for 2 h, when TLC (8:2 hexane:Et$_2$O) indicated that the reaction had gone to completion. To the reaction mixture was added a saturated aqueous solution of NH$_4$Cl (100 mL) and allowed to warm to RT over 16 h. The reaction mixture was extracted with Et$_2$O (2×200 mL), and the combined organic phase washed with brine (50 mL), dried (MgSO$_4$) and evaporated in vacuo. The residue was purified by silica gel column chromatography, eluted with hexane/Et$_2$O (8:2) to afford the title compounds as a light yellow oil (1.91 g, 91%). $^1$H-NMR (d$_6$-DMSO, 250 MHz): δ 0.44-0.58 (m, 3H, —NHCH(CH$_2$CH$_3$)CH(CH$_3$)OH), 0.99-1.12 (m, 5H, —NHCH(CH$_2$CH$_3$)CH(CH$_3$)OH+—NHCH(CH$_2$CH$_3$)CH(CH$_3$)OH), 2.03 (m, 1H, —NHCH(CH$_2$CH$_3$)CH(CH$_3$)OH), 3.32-3.51 (m, 1H, —NHCH(CH$_2$CH$_3$)CH(CH$_3$)OH), 4.40 (d, 1H, J=3.79 Hz, —NHCH(CH$_2$CH$_3$)CH(CH$_3$)OH), 7.14-7.51 (m, 15H, 3×Bz).

(2R, 3S)-3-(Trityl-amino)-pentan-2-ol

To a stirred suspension of CuBr.SMe$_2$ (2.74 g, 13.33 mmol) in Et$_2$O (100 mL) under Ar at −70° C., was added methyl lithium (1:6 M in Et$_2$O; 15.13 mL, 24.21 mmol) dropwise and the solution allowed to warm to RT. The mixture was re-cooled to −70° C., to which was added a solution of (S)-2-(trityl-amino)-butyraldehyde (2 g, 6.05 mmol) in Et$_2$O (25 mL) dropwise with stirring. The reaction mixture was stirred at this temperature for 2 h and then at −55° C. for 4 h, when TLC (8:2 hexane/Et$_2$O) indicated that the reaction had gone to completion. To the reaction mixture was added a saturated aqueous solution of NH$_4$Cl (100 mL) and allowed to warm to RT over 16 h. The reaction mixture was extracted with Et$_2$O (2×200 mL), and the combined organic phase washed with brine (50 mL), dried (MgSO$_4$) and evaporated in vacuo. The residue was purified by silica gel column chromatography, eluted with hexane/Et$_{20}$ (8:2) to afford the title compounds as a light yellow oil (1.37 g, 66%). $^1$H-NMR (d$_6$-DMSO, 250 MHz): δ 0.44-0.58 (m, 3H, —NHCH(CH$_2$CH$_3$)CH(CH$_3$)OH), 0.99-1.12 (m, 5H, —NHCH(CH$_2$CH$_3$)CH(CH$_3$)OH+—NHCH(CH$_2$CH$_3$)CH(CH$_3$)OH), 2.01 (m, 1H, —NHCH(CH$_2$CH$_3$)CH(CH$_3$)OH), 3.22-3.43 (m, 1H, —NHCH(CH$_2$CH$_3$)CH(CH$_3$)OH), 4.41 (d, 1H, J=3.31 Hz, —NHCH(CH$_2$CH$_3$)CH(CH$_3$)OH), 7.14-7.56 (m, 15H, 3×Bz).

(2RS,3R)-3-(Trityl-amino)-pentan-2-ol

To a stirred solution of (R)-2-(trityl-amino)-butyraldehyde (0.59 g, 1.79 mmol) in Et$_2$O (25 mL) under Ar at −70° C., was added methyl lithium (1.4 M in Et$_2$O; 1.88 mL, 2.63 mmol) dropwise. The reaction mixture was stirred at this temperature for 30 min and then allowed to warm to RT over 15 min and stirred at this temperature for 1 h. The mixture was cooled to 0° C. to which was slowly added H$_2$O (25 mL) and the solution was extracted between Et$_2$O (100 mL) and H$_2$O (100 mL). The aqueous phase was extracted with more Et$_2$O (2×50 mL), and the combined organic phase was washed with brine (50 mL), dried (MgSO$_4$) and evaporated in vacuo to afford the title compounds as a light yellow oil (0.58 g, 94%). $^1$H-NMR (d$_6$-DMSO, 250 MHz): δ 0.42-0.57 (m, 3H, —NHCH(CH$_2$CH$_3$)CH(CH$_3$)OH), 0.97-1.15 (m, 5H, —NHCH(CH$_2$CH$_3$)CH(CH$_3$)OH+—NHCH(CH$_2$CH$_3$)CH(CH$_3$)OH), 2.01 (m, 1H, —NHCH(CH$_2$CH$_3$)CH(CH$_3$)OH), 3.26 (m, 1H, —NHCH(CH$_2$CH$_3$)CH(CH$_3$)OH), 4.39 (d, 1H, J=4.10 Hz, —NHCH(CH$_2$CH$_3$)CH(CH$_3$)OH), 7.13-7.50 (m, 15H, 3×Bz).

(2S, 3R;-3-Amino-pentan-2-ol

To a stirred solution of (2S,3R)-3-(trityl-amino)-pentan-2-ol (1.32 g, 3.83 mmol) in CH$_2$Cl$_2$ (50 mL) under Ar at RT, was added trifluoroacetic acid (10 mL) dropwise, and the solution was stirred at this temperature for 1 h. The solvent was evaporated in vacuo and the residue was precipitated from Et$_2$O (15 mL) with hexane (300 mL) with stirring to give a yellow oil. The solvent was decanted from the oil, and the oil was washed with hexane (30 mL) and dried in vacuo to afford the title compound as a light yellow oil (0.30 g, 99%; 80% de). $^1$H-NMR (d$_6$-DMSO, 250 MHz): δ 0.915+0.924 (2×t [1:5, 2R/3R:2R/3S], 3H, J=7.50+7.58 Hz, NH$_2$CH(CH$_2$CH$_3$)CH(CH$_3$)OH), 1.06+1.13 (2×d [5:1, 2'R/3'S:2'R/3'R], J=6.48+6.32 Hz), NH$_2$CH(CH$_2$CH$_3$)CH(CH$_3$)OH), 1.41-1.59 (m, 2H$_1$, NH$_2$CH(CH$_2$CH$_3$)CH(CH$_3$)OH), 2.77+2.93 (2×m, 1H, [1:5, 2'R/3'R:2'R/3'S], NH$_2$CH(CH$_2$CH$_3$)CH(CH$_3$)OH), 3.62-3.72+3.80-3.90 (2×m, 1H, [1:5, 2'R/3'R:2'R/3'S] NH$_2$CH(CH$_2$CH$_3$)CH(CH$_3$)OH), 7.75 (bs, 2H, NH$_2$).

(2R,3S)-3-Amino-pentan-2-ol

To a stirred solution of (2R,3S)-3-(trityl-amino)-pentan-2-ol (1.64 g, 4.75 mmol) in CH$_2$Cl$_2$ (50 mL) under Ar at RT, was added trifluoroacetic acid (10 mL) dropwise, and the solution was stirred at this temperature for 1 h. The solvent was evaporated in vacuo and the residue was precipitated from Et$_2$O (15 mL) with hexane (300 mL) with stirring to give a yellow oil. The solvent was decanted from the oil, and the oil was washed with hexane (30 mL) and dried in vacuo to afford the title compound as a light yellow oil (0.30 g, 98%; 80% de). $^1$H-NMR (d$_6$-DMSO, 250 MHz): δ 0.913+0.923 (2×t [1:5, 2'S/3'S:2'S/3'R], 3H, J=7.50+7.50 Hz, NH$_2$CH(CH$_2$CH$_3$)CH(CH$_3$)OH), 1.11+1.18 (2×d [5:1, 2'S/3'R:2'S/3'S], J=6.48+6.48 Hz), NH$_2$CH(CH$_2$CH$_3$)CH(CH$_3$)OH), 1.41-1.65 (m, 2H, NH$_2$CH(CH$_2$CH$_3$)CH(CH$_3$)OH), 2.76+2.93 (2×m, 1H, [1:5, 2'S/3'S:2'S/3'R], NH$_2$ CH(CH₂CH₃)CH(CH₃)OH), 3.61-3.69+3.80-3.90 (2×m, 1H, [1:5, 2'S/3'S:2'S/3'R], NH₂CH(CH₂CH₃)CH(CH₃)OH), 7.73 (bs, 2H, NH₂).

(2RS,3R)-3-Amino-pentan-2-ol

To a stirred solution of (2RS,3R)-3-(trityl-amino)-pentan-2-ol (0.55 g, 1.59 mmol) in CH₂Cl₂ (25 mL) under Ar at RT, was added trifluoroacetic acid (12 mL) dropwise, and the solution was stirred at this temperature for 2 h. The solvent was evaporated in vacuo and the residue was precipitated from Et₂O (15 mL) with hexane (300 mL) with stirring to give a yellow oil. The solvent was decanted from the oil, and the oil was washed with hexane (30 mL) and dried in vacuo to afford the title compound as a brown oil (0.16 g, 99%). ¹H-NMR (d₆-DMSO, 250 MHz): δ 0.86-0.96 (m, 3H, NH₂CH(CH₂CH₃)CH(CH₃)OH), 1.02-1.20 (m, 3H, NH₂CH(CH₂CH₃)CH(CH₃)OH), 1.35-1.68 (m, 2H, NH₂CH(CH₂CH₃)CH(CH₃)OH), 2.75+2.91 (2×m, 1H, NH₂CH(CH₂CH₃)CH(CH₃)OH), 3.60-3.70+3.78-3.88 (m, 1H, NH₂CH(CH₂CH₃)CH(CH₃)OH), 7.68 (bs, 2H, NH₂).

(2S, 3R)-3-(6-Benzylamino-9-isopropyl-9H-purin-2-ylamino)-pentan-2-ol

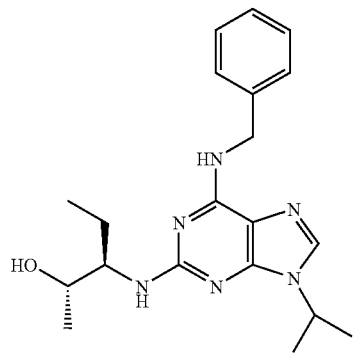

To a stirred solution of benzyl-(2-fluoro-9-isopropyl-9H-purin-6-yl)-amine (0.20 g, 0.70 mmol) in Bu″OH/DMSO (5 mL, 4:1) at RT under Ar was added Pr$^i$₂NEt (1.2 mL, 6.88 mmol) followed by (2S,3R)-3-amino-pentan-2-ol (0.18 g, 1.74 mmol). The reaction mixture was placed in a preheated oil bath at 140° C. and stirred at this temperature for 72 h, when TLC (55:40:5, CH₂Cl₂/Et₂O/MeOH) indicated that the reaction had gone to completion. The reaction mixture was allowed to cool to RT and the solvent was evaporated in vacuo. The residue was partitioned between CH₂Cl₂ (100 ML) and H₂O (200 mL), the aqueous phase was extracted with more CH₂Cl₂ (3×50 mL), and the combined organic phase was washed with brine (50 mL), dried (MgSO₄) and evaporated in vacuo. The residue was purified by gradient column chromatography on silica gel eluted with CH₂Cl₂/Et₂O/MeOH (60:40:0→60:40:2) to afford the title compound as a white solid (0.11 g, 43%, 80% de). Mp 42-44° C. ¹H-NMR (d₆-DMSO, 250 MHz): δ 0.81 (m, 3H, —NHCH(CH₂CH₃)CH(CH₃)OH), 1.02 (d, 3H, J=6.16 Hz, —NHCH(CH₂CH₃)CH(CH₃)OH) 1.45 (m, 8H, —NHCH(CH₂CH₃)CH(CH₃)OH+—CH(CH₃)₂), 3.62+3.73 (2×m, 1H, —NHCH(CH₂CH₃)CH(CH₃)OH), 4.49-4.63 (m, 4H, —HNCH₂-Bz+—NHCH(CH₂CH₃)CH(CH₃)OH+—CH(CH₃)₂), 5.59+5.90 ([1:8, 2'R/3'S:2'R/3'S], 2×d, 1H, J=9.00+8.85 Hz, —NHCH(CH₂CH₃)CH(CH₃)OH), 7.19-7.37 (m, 5H, Bz), 7.77 (bs, 2H, —N=CH—N—+—HNCH₂-Bz). FAB-MS m/z (relative intensity): 369 ([M+H]⁺, 100), 323 (70), 134 (15). Accurate Mass (M+H): Actual: 369.2403, Measured: 369.2418.

(2R,3S)-3-(6-Benylamino-9-isopropyl-9H-purin-2-ylamino)-pentan-2-ol

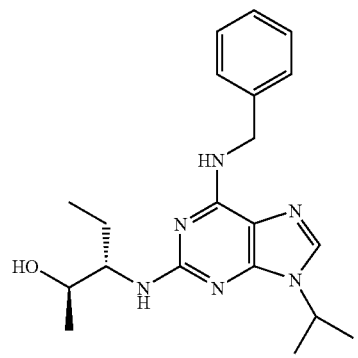

To a stirred solution of benzyl 2-fluoro-9-isopropyl-9H-purin-6-yl)-amine (0.20 g, 0.70 mmol) in Bu″OH/DMSO (5 mL, 4:1) at RT under Ar was added Pr$^i$₂NEt (1.2 mL, 6:88 mmol) followed by (2R,3S)-3-amino-pentan-2-ol (0.20 g, 1.94 mmol). The reaction mixture was placed in a preheated oil bath at 140° C. and stirred at this temperature for 48 h, when TLC (55:40:5 CH₂Cl₂/Et₂O/MeOH) indicated that the reaction had gone to completion. The reaction mixture was allowed to cool to RT and the solvent was evaporated in vacuo. The residue was partitioned between CH₂Cl₂ (100 mL) and H₂O (200 mL), the aqueous phase was extracted with more CH₂Cl₂ (3×50 mL), and the combined organic phase was washed with brine (50 mL), dried (MgSO₄) and evaporated in vacuo. The residue was purified by gradient column chromatography on silica gel eluted with CH₂Cl₂/Et₂O/MeOH (60:40:0→60:40:2) to afford the title compound as a white solid (0.11 g, 43%, 88% de). Mp 48-50° C. ¹H-NMR (d₆-DMSO, 250 MHz): δ 0.78-0.87 (m, 3H, —NHCH(CH₂CH₃)CH(CH₃)OH), 1.02 (d, 3H, J=6.16 Hz, —NHCH(CH₂CH₃)CH(CH₃)OH 1.43-1.75 (m, 8H, —NHCH(CH₂CH₃)CH(CH₃)OH+—CH(CH₃)₂), 3.62+3.76 (2×m, 1H, —NHCH(CH₂CH₃)CH(CH₃)OH), 4.48-4.64 (m, 4H, —HNCH₂-Bz+—NHCH(CH₂CH₃)CH(CH₃)OH+—CH(CH₃)₂), 5.59+5.88 ([1:8, 2'S/3'S:2'S/3'R], 2×d, 1H, J=9.48+8.69 Hz, —NHCH(CH₂CH₃)CH(CH₃)OH), 7.19-7.37 (m, 5H, Bz), 7.77 (bs, 2H; —N=CH—N—+—HNCH₂-Bz). FAB-MS m/z (relative intensity): 369 ([M+H]⁺, 100), 323 (68), 154 (30), 136 (30). Accurate Mass (M+H): Actual: 369.2403, Measured: 369.2418. Microanalysis (Expected:Measured) C₂₀H₂N₆O.0.4H₂O: C, 63.94:64.56; H, 7.73:7.73; N, 22.37:21.92.

(2RS, 3R)-3-(6-Benzylamino-9-isopropyl-9H-purin-2-ylamino)-pentan-2-ol

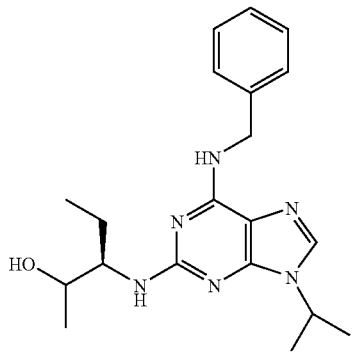

To a stirred solution of benzyl-(2-fluoro-9-isopropyl-9H-purin-6-yl)-amine (0.34 g, 1.19 mmol) in Bu"OH/DMSO (5 mL, 4:1) at RT under Ar was added Pr$^i_2$NEt (2.0 mL, 11.48 mmol) followed by (2RS,3R)-3-amino-pentan-2-ol (0.16 g, 1.55 mmol). The reaction mixture was placed in a preheated oil bath at 140° C. and stirred at this temperature for 48 h, when TLC (55:40:5 CH$_2$Cl$_2$ Et$_2$O/MeOH) indicated the appearance of a lower running product together with some desired product. The reaction mixture was allowed to cool to RT and the solvent was evaporated in vacuo. The residue was partitioned between CH$_2$Cl$_2$ (100 mL) and H$_2$O (200 mL), the aqueous phase was extracted with more CH$_2$Cl$_2$ (3×50 mL), and the combined organic phase was washed with brine (50 mL), dried (MgSO$_4$) and evaporated in vacuo. The residue was purified by gradient column chromatography on silica gel eluted with CH$_2$Cl$_2$/Et$_2$O/MeOH (60:40:0→60:40:4) to afford thee title compound as a white solid (0.03 g, 7%). Mp 43-46° C. $^1$H-NMR (d$_6$-DMSO, 250 MHz): δ 0.75-0.85 (m, 3H, —NHCH(CH$_2$CH$_3$)CH(CH$_3$)OH), 0.95-1.03 (m, 3H, —NHCH(CH$_2$CH$_3$)CH(CH$_3$)OH) 1.19-1.77 (m, 8H, —NHCH(CH$_2$CH$_3$)CH(CH$_3$)OH+CH(CH$_3$)$_2$), 3.60+3.73 (2×m, 1H, —NHCH(CH$_2$CH$_3$)CH(CH$_3$)OH), 4.44-4.78 (m, 4H, —HNCH$_2$-Bz+—NHCH(CH$_2$CH$_3$)CH(CH$_3$)OH+—CH(CH$_3$)$_2$), 5.57+5.87 (2×d, 1H, J=9.958+7.74 Hz, —NHCH(CH$_2$CH$_3$)CH(CH$_3$)OH), 7.18-7.36 (m, 5H, Bz), 7.77 (bs, 2H, —N=CH—N—+—HNCH$_2$-Bz). FAB-MS m/z (relative intensity): 369 ([M+H]$^+$, 100), 323 (96), 233 (30). Accurate Mass (M+H): Actual: 369.2403, Measured: 369:2393 Microanalysis (Expected:Measured) C$_{20}$H$_{28}$N$_6$O.0.5H$_2$O: C, 63.64:64.17; H, 7.74:7.56; N, 22.26: 21.38.

Example 8

(R)-2-(6-Benzylamino-9-isopropyl-9H-purin-2-ylamino)-butyric acid

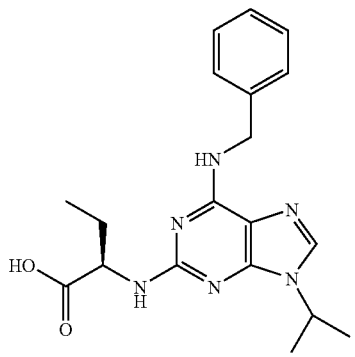

Benzyl-(2-fluoro-9-isopropyl-9H-purin-6-yl)-amine (151 mg, 0.5 mmol) was dissolved in NMP (5 mL) and DBU (1.5 mL, 10 mmol). (R)-(−)-2-Aminobutyric acid (99% ee/GLC; 1.03 g, 10 mmol) was then added and the mixture was stirred under N$_2$ at 160° C. for 1 h. After cooling, the mixture was diluted with citric acid (10% aq solution) and CH$_2$Cl$_2$ (25 mL each). The phases were separated and the organic fraction was extracted with brine (2×10 mL), dried over MgSO$_4$, filtered, and evaporated. The residue was redissolved in MeCN and was fractionated by preparative RP-HPLC (Vydac 218TP1022, 9 mL/min, 22.5-32.5% MeCN in H$_2$O containing 0.1% CF$_3$COOH over 40 min). Appropriate fractions were pooled and lyophilised to afford the pure title compound (137 mg, 74.4%) as an amorphous off-white solid. Anal. RP-HPLC (Vydac 218TP54, 1 mL/min): t$_R$=16.04 min (0-60% MeCN), 15.95 min (22.5-32.5% MeCN in H$_2$O containing 0.1% CF$_3$COOH over 20 min), purity: >98% (λ=214 nm). $^1$H-NMR (d$_6$-DMSO, 300 MHz) δ: 0.95 (t, J=7.3 Hz, 3H, CH$_2$CH$_3$); 1.51 (d, J=6.7 Hz, 6H, CH(CH$_3$)$_2$); 1.78 (m, J=7.3 Hz, 2H, CH$_2$CH$_3$); 4.27 (m, 1H, CHCH2); 4.64 (hept., J=6.7 Hz, 1H, CH(CH$_3$)$_2$); 4.69 (m, 2H, CH$_2$Ph); 7.25-7.41 (m, 6H, ArH). DE-MALDI-TOF MS (α-cyano-hydroxy-cinnamic acid matrix): [M+H]$^+$=369.41. FAB-MS: [M+H]$^+$ =369.2033 (C$_{19}$H$_{25}$N$_6$O$_2$ requires 369.2039).

Example 9

(3RS,4R)-4-(6-Benzylamino-9-isopropyl-9H-purin-2-ylamino)-hexan-3-ol

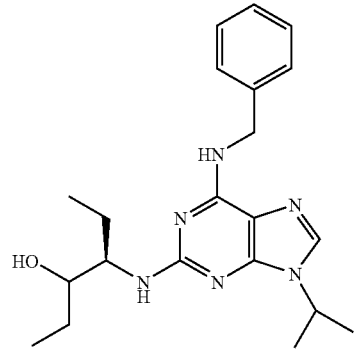

(3RS,4R)-4-(Trityl-amino)-hexan-3-ol

To a stirred solution of (R)-2-(trityl-amino)-butyraldehyde (1.5 g, 1 eq, 4.53 mmol) in ether (150 mL) under an argon atmosphere at −78° C., was added ethylmagnesium bromide (3 M in ether, 1.51 mL, 1 eq, 4.53 mmol) dropwise. The solution was sired at −78° C. for 2 h, then allowed to warm to room temperature over 16 h. The mixture was re-cooled to 0° C., H$_2$O (150 mL) added, and the organic phase separated. The aqueous phase was extracted with more ether (2×50 mL), and the combined organic phase washed with brine (50 mL), dried (MgSO$_4$) and evaporated in vacuo. The residue was purified by silica gel column chromatography, eluted with hexane:ether (90:10) to afford the title compound as a light yellow oil; Yield: 1.13 g (69%): (57% A de 3S,4R: 43% de 3R,4R). $^1$H-NMR (d$_6$-DMSO, 250 MHz): δ 0.45+0.69 (t+m, 6H, J=7.43 Hz, —NHCH(CH$_2$CH$_3$)CH(CH$_2$CH$_3$)OH), 1.12-1.29 (m, 4H, —NHCH(CH$_2$CH$_3$)CH(CH$_2$CH$_3$)OH), 2.16 (m, 1H, —NHCH(CH$_2$CH$_3$)CH(CH$_2$CH$_3$)OH), 2.54 (m, 1H, —NHCH(CH$_2$CH$_3$)CH(CH$_2$CH$_3$)OH), 3.21-3.40 (m, 1H, —NHCH(CH$_2$CH$_3$)CH(CH$_2$CH$_3$)OH), 4.29+4.39 (2×d, 1H, J=4.42+5.37 Hz, —NHCH(CH$_2$CH$_3$)CH(CH$_2$CH$_3$)OH), 7.15-7.52 (m, 15H, 3×Bz).

(3RS,4R)-4-Amino-hexan-3-ol

To a stirred solution of (3RS,4R)-4-(trityl-amino)-hexan-3-ol (1.13 g, 1 eq, 3.14 mmol) in DCM (15 mL) under an argon atmosphere at room temperature, was added trifluoroacetic acid (7 mL) dropwise, and the solution was stirred at this temperature for 4 h. The solvent was evaporated in vacuo, EtOH (20 mL) added, and removed in vacuo, and this process repeated a further two times. The residue was precipitated from ether (5 mL) with hexane (40 mL) with stirring to give a yellow oil: The solvent was decanted from the oil, and the oil was washed with hexane (30 mL) and dried in vacuo to afford the title compound as a light yellow oil; Yield: 0.37 g (100%). (57% de 3S,4R: 43% de 3R,4R). $^1$H-NMR (d$_6$-DMSO, 250 MHz): δ 0.79+0.92 (t+m, 6H, J=7.42 Hz, NH$_2$CH(CH$_2$CH$_3$)CH(CH$_2$CH$_3$)OH), 1.30-1.67 (m, 4H, NH$_2$CH(CH$_2$CH$_3$)CH(CH$_2$CH$_3$)OH), 2.70 (m, 1H, NH$_2$CH(CH$_2$CH$_3$)CH(CH$_2$CH$_3$)OH), 2.84+2.96 (2×m, 1H, NH$_2$CH(CH$_2$CH$_3$)CH(CH$_2$CH$_3$)OH), 3.41+3.56 (2×m, 1H, NH$_2$CH(CH$_2$CH$_3$)CH(CH$_2$CH$_3$)OH), 7.71 (bs, 2H, NH$_2$CH(CH$_2$CH$_3$)CH(CH$_2$CH$_3$)OH).

(3RS,4R)-4-(6-Benzylamino-9-isopropyl-9H-purin-2-ylamino)-hexan-3-ol

To a stirred solution of benzyl-(2-fluoro-9-isopropyl-9H-purin-6-yl)-amine (40 mg, 1 eq, 0.14 mmol) in n-BuOH/DMSO (3.75 mL, 4:1) at room temperature under an argon atmosphere was added DIEA (0.24 mL, 9.8 eq, 1.38 mmol) followed by (3RS,4R)-4-amino-hexan-3-ol (110 mg, 6.7 eq, 0.93 mmol). The reaction mixture was placed in a preheated oil bath at 140° C. and stirred at this temperature for 72 h, when TLC DCM:ether:MeOH (55:40:5) indicated that the reaction had gone to completion The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×50 mL), and the combined organic phase was washed with brine (50 mL), dried (MgSO$_4$) and evaporated in vacuo. The residue was purified by gradient column chromatography on silica gel eluted with hexane:ether:MeOH (50:50:0→50:50:2) to afford the title compound as a white solid; Yield: 31 mg (58%).(57% de 4R,3S: 43% de 4R,3R). $^1$H-NMR (d-CDCl$_3$, 250 MHz): δ 0.92-1.08 (m, 6H, —NHCH(CH$_2$CH$_3$)CH(CH$_2$CH$_3$)OH), 1.56 (d, 6H, J=6.79 Hz, —CH(CH$_3$)$_2$), 1.44-1.69 (m, 4H, —NHCH(CH$_2$CH$_3$)CH(CH$_2$CH$_3$)OH), 3.45 (d, 1H, J=6.32 Hz, OH) 3.56-3.70 (m, 1H, —NHCH(CH$_2$CH$_3$)CH(CH$_2$CH$_3$)OH), 3.91-4.06 (m, 1H, —NHCH(CH$_2$CH$_3$)CH(CH$_2$CH$_3$)OH), 4.58-4.69 (m, 1H, —CH(CH$_3$)$_2$), 4.73-5.01 (m, 2H, —HNCH$_2$-Bz), 5.16-5.32+6.01-6.22 (2×m, 1H, —NHCH(CH$_2$CH$_3$)CH(CH$_2$CH$_3$)OH), 7.22-7.43 (m, 6H, 5×Bz-H+HNCH$_2$-Bz), 7.52 (s, 1H, —N═CH—N). FABMS m/z (relative intensity): 383 ([M+H]$^+$, 100), 323 (55), 296 (21). Accurate Mass (M+H): Actual: 383.2559, Measured: 383.2542.

Example 10

(3RS,4S)-4-(6-Benzylamino-9-isopropyl-9H-purin-2-ylamino-hexan-3-ol

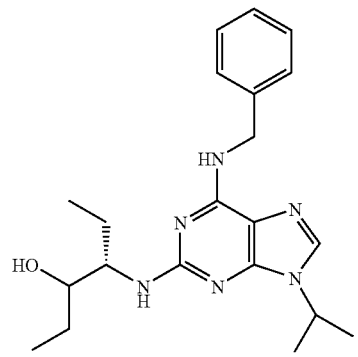

(3RS,4S)-4-(Trityl-amino)-hexan-3-ol

To a stirred solution of (S)-2-(trityl-amino)-butyraldehyde (1.5 g, 1 eq, 4.53 mmol) in ether (150 mL) under an argon atmosphere at −78° C., was added ethylmagnesium bromide (3 M in ether, 1.51 mL, 1 eq, 4.53 mmol) dropwise. The solution was stirred at −78° C. for 2 h, then allowed to warm to room temperature over 16 h. The mixture was re-cooled to 0° C., H$_2$O (150 mL) added, and the organic phase separated. The aqueous phase was extracted with more ether (2×50 mL), and the combined organic phase washed with brine (50 mL), dried (MgSO$_4$) and evaporated in vacuo. The residue was purified by silica gel column chromatography, eluted with hexane:ether (90:10) to afford the title compound as a light yellow oil; Yield: 1.19 g (73%). (65% de 3R,4S: 35% de 3S,4S) $^1$H-NMR(d$_6$-DMSO, 250 MHz): δ 0.46+0.69 (t+m, 6H, J=7.34 Hz, —NHCH(CH$_2$CH$_3$)CH(CH$_2$CH$_3$)OH), 1.13-1.29 (m, 4H, —NHCH(CH$_2$CH$_3$)CH(CH$_2$CH$_3$)OH), 2.17 (m, 1H, —NHCH(CH$_2$CH$_3$)CH(CH$_2$CH$_3$)OH), 2.55 (m, 1H, —NHCH(CH$_2$CH$_3$)CH(CH$_2$CH$_3$)OH), 3.20-3.39 (m, 1H, —NHCH(CH$_2$CH$_3$)CH(CH$_2$CH$_3$)OH), 4.29+4.39 (2×d, 1H, J=4.74+5.53 Hz, —NHCH(CH$_2$CH$_3$)CH(CH$_2$CH$_3$)OH), 7.15-7.52 (m, 15H, 3×Bz).

(3RS,4S)-4-Amino-hexan-3-ol

To a stirred solution of (3RS,4S)-4-(trityl-amino)-hexan-3-ol (1.19 g, 1 eq, 3.31 mmol) in DCM (15 mL) under an argon atmosphere at room temperature, was added trifluoroacetic acid (7 mL) dropwise, and the solution was stirred at this temperature for 4 h. The solvent was evaporated in vacuo, EtOH (20 mL) added, and removed in vacuo, and this process repeated a further two times. The residue was precipitated from ether (5 mL) with hexane (40 mL) with stirring to give a yellow oil. The solvent was decanted from the oil, and the oil was washed with hexane (30 mL) and dried in vacuo to afford the title compound as a light yellow oil; Yield: 0.39 g (99%). (65% de 3R,4S: 35% de 3S,4S). $^1$H-NMR (d$_6$-DMSO, 250 MHz): δ 0.79+0.92 (t+m, 6H, J=7.50 Hz, NH$_2$CH(CH$_2$CH$_3$)CH(CH$_2$CH$_3$)OH), 1.22-1.68 (m, 4H, NH$_2$CH(CH$_2$CH$_3$)CH(CH$_2$CH$_3$)OH), 2.71 (m, 1H, NH$_2$CH(CH$_2$CH$_3$)CH(CH$_2$CH$_3$)OH), 2.83+2.95 (2×m, 1H, NH$_2$CH(CH$_2$CH$_3$)CH(CH$_2$CH$_3$)OH), 3.39+3.54 (2×m, 1H, NH$_2$CH(CH$_2$CH$_3$)CH(CH$_2$CH$_3$)OH), 7.77 (bs, 2H, NH$_2$CH(CH$_2$CH$_3$)CH(CH$_2$CH$_3$)OH).

(3RS,4S)-4-(6-Benzylamino-9-isopropyl-9H-purin-2-ylamino)-hexan-3-ol

To a stirred solution of benzyl-(2-fluoro-9-isopropyl-9H-purin-6-yl)-amine (40 mg, 1 eq, 0.14 mmol) in n-BuOH/DMSO (3.75 mL, 4:1) at room temperature under an argon atmosphere was added DIEA (0.24 mL, 9.8 eq, 1.38 mmol) followed by (3RS,4)-4-amino-hexan-3-ol (110 mg, 6.7 eq, 0.93 mmol). The reaction mixture was placed in a preheated oil bath at 140° C. and stirred at this temperature for 72 h, when TLC DCM:ether:MeOH (55:40:5) indicated that the reaction had gone to completion. The reaction mixture was allowed to cool to room temperature and the solvent was evaporated in vacuo. The residue was partitioned between EtOAc (50 mL) and brine/water(1:1, 100 mL), the aqueous phase was extracted with more EtOAc (2×50 mL), and the combined organic phase was washed with brine (50 mL), dried (MgSO$_4$) and evaporated in vacuo. The residue was purified by gradient column chromatography on silica gel eluted with hexane:ether:MeOH (50:50:0→50:50:2) to afford the title compound as a white solid; Yield: 32.5 mg (61%).(57% de 4S,3R: 43% de 4S,3S). $^1$H-NMR (d-CDCl$_3$, 250 MHz): δ 0.85-1.08 (m, 6H, —NHCH(CH$_2$CH$_3$)CH(CH$_2$CH$_3$)OH), 1.56 (d, 6H, J=6.79 Hz, +—CH(CH$_3$)$_2$), 1.44-1.66 (m, 4H, —NHCH(CH$_2$CH$_3$)CH(CH$_2$CH$_3$)OH), 3.45 (d, 1H, J=6.32 Hz, OH), 3.54-3.71 (m, 1H, —NHCH(CH$_2$CH$_3$)CH(CH$_2$CH$_3$)OH), 3.91-4.05 (m, 1H, —NHCH(CH$_2$CH$_3$)CH(CH$_2$CH$_3$)OH), 4.58-4.70 (m, 1H, —CH(CH$_3$)$_2$), 4.73-4.89 (m, 2H, —HNCH$_2$-Bz), 5.16-5.32+6.01-6.25 (2×m, 1H, —NHCH(CH$_2$CH$_3$)CH(CH$_2$CH$_3$)OH), 7.24-7.43 (m, 6H, 5×Bz-H+HNCH$_2$-Bz), 7.54 (s, 1H, —N=CH—N). FABMS m/z (relative intensity): 383 ([M+H]$^+$, 100), 323 (60), 295 (15). Accurate Mass (M+H): Actual: 383.2559, Measured: 383.2542.

Example 11

(3RS,4R)-4-(6-Benzylamino-9-isopropyl-9H-purin-2-ylamino)-2-methyl-hexan-3-ol

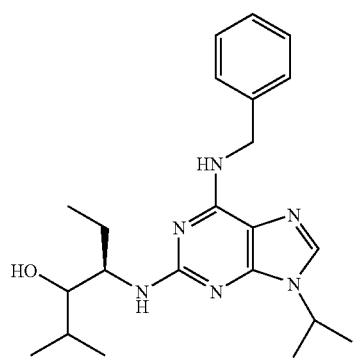

(3RS,4R)-2-Methyl-4-(trityl-amino)-hexan-3-ol

To a stirred suspension of CuBr.SMe$_2$ (1.37 g, 2.2 eq, 6.66 mmol) in ether (100 mL) under an argon atmosphere at −78° C., was added isopropyllithium (0.7 M in pentane, 17.29 mL, 4 eq, 12.1 mmol) dropwise, and the solution allowed to warm to room temperature. The mixture was recooled to −70° C., to which was added a solution of (R)-2-(trityl-amino)-butyraldehyde (1 g, 1 eq, 3.03 mmol) in ether (25 mL) dropwise with stirring. The reaction mixture was stirred at this temperature for 1 h, then allowed to warm to −55° C. and stirred at this temperature for 3 h. To the reaction mixture was added a saturated aqueous solution of NH$_4$Cl (100 mL) and allowed to warm to room temperature over 16 h The reaction mixture was extracted with ether (2×200 mL), and the combined organic phase washed with brine (50 mL), dried (MgSO$_4$) and evaporated in vacuo. The residue was purified by silica gel gradient column chromatography, eluted with hexane:ether (100:0→90:10) to afford the title compound as a colourless oil; Yield: 0.53 g (47%). (50% de 3S,4R: 50% de 3R,4R) $^1$H-NMR (d$_6$-DMSO, 250 MHz): δ 0.44 (t, 3H, J=7.03 Hz, —NHCH(CH$_2$CH$_3$)CH(CH(CH$_3$)$_2$)OH), 0.52+0.77 (2×d, 6H, J=6.48 Hz, —NHCH(CH$_2$CH$_3$)CH(CH(CH$_3$)$_2$)OH), 0.79-1.13 (m, 2H, —NHCH(CH$_2$CH$_3$)CH(CH(CH$_3$)$_2$)OH), 1.72 (m, 1H, —NHCH(CH$_2$CH$_3$)CH(CH(CH$_3$)$_2$)OH, 2.11 (m, 1H, —NHCH(CH$_2$CH$_3$)CH(CH(CH$_3$)$_2$)OH), 2.77 (m, 1H, —NHCH(CH$_2$CH$_3$)CH(CH(CH$_3$)$_2$)OH), 2.99 (m, 1H, —NHCH(CH$_2$CH$_3$)CH(CH(CH$_3$)$_2$)OH), 4.55 (d, 1H, J=5.21 Hz, —NHCH(CH$_2$CH$_3$)CH(CH(CH$_3$)$_2$)OH), 7.15-7.46 (m, 15H, 3×Bz).

(3RS,4R)-4-Amino-2-methyl-hexan-3-ol

To a stirred solution of (3RS,4R)-2-methyl-4-(trityl-amino)-hexan-3-ol (0.53 g, 1 eq, 1.41 mmol) in DCM (2 mL)-under an argon atmosphere at room temperature, was added trifluoroacetic acid (5 mL) dropwise, and the solution was stirred at this temperature for 1 h. The solvent was evaporated in vacuo, the residue was precipitated from ether (10 mL) with hexane (90 mL) with stirring to give a yellow oil. The solvent was decanted from the oil, and the oil was washed with hexane (20 mL) and dried in vacuo to afford the title compound as a light yellow oil; Yield: 0.18 g (100%). (50% de 3S,4R: 50% de 3R,4R). $^1$H-NMR ($_6$-DMSO, 250 MHz): δ 0.85-0.99 (m, 9H, NH$_2$CH(CH$_2$CH$_3$)CH(CH(CH$_3$)$_2$)OH), 1.42-1.79 (m, 2H, NH$_2$CH(CH$_2$CH$_3$)CH(CH(CH$_3$)$_2$)OH), 2.95 (m, 1H, NH$_2$CH(CH$_2$CH$_3$)CH(CH(CH$_3$)$_2$)OH), 3.18 (m, 1H, NH$_2$CH(CH$_2$CH$_3$)CH(CH(CH$_3$)$_2$)OH), 3.37 (m, 1H, NH$_2$CH(CH$_2$CH$_3$)CH(CH(CH$_3$)$_2$)OH), 7.58 (bs, 2H, NH$_2$CH(CH$_2$CH$_3$)CH(CH(CH$_3$)$_2$)OH).

(3RS,4R)-4-(6-Benzylamino-9-isopropyl-9H-purin-2-ylamino)-2-methyl-hexan-3-ol To a stirred solution of benzyl-2-fluoro-9-isopropyl-9H-purin-6-yl)-amine (40 mg, 1 eq, 0.14 mmol) in n-BuOH/DMSO (2.5 mL, 4:1) at room temperature under an argon atmosphere was added DIEA (0.12 mL, 4.9 eq, 0.69 mmol) followed by (3RS,4R)-4-amino-2-methyl-hexan-3-ol (54 mg, 2.9 eq, 0.41 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×50 mL), and the combined organic phase was washed with brine (50 mL), dried (MgSO$_4$) and evaporated in vacuo. The residue was purified by gradient column chromatography on silica gel eluted with hexane:ether:MeOH (50:50:0→50:50:2) to afford the title compound as a white solid, Yield: 8.8 mg (16%). (50% de 4R,3S: 50% de 4R,3R). $^1$H-NMR (d-CDCl$_3$, 250 MHz): δ 0.96-1.04 (m, 9", —NHCH(CH$_2$CH$_3$)CH(CH(CH$_3$)$_2$)OH), 1.57 (d, 6H, J=6.63 Hz, —CH(CH$_3$)$_2$), 1.68-2.19 (m, 4H, —NHCH(CH$_2$CH$_3$)CH(CH(CH$_3$)$_2$)OH), 3.24-3.32 (m, 1H, —NHCH(CH$_2$CH$_3$)CH(CH(CH$_3$)$_2$)OH), 3.86-4.01 (m, 1H, —NHCH(CH$_2$CH$_3$)CH(CH(CH$_3$)$_2$)OH), 4.57-4.70 (m, 1H, —CH(CH$_3$)$_2$), 4.76-4.93 (m, 2H, —HNCH$_2$-Bz), 5.33-5.60 (m, 1H, —NHCH(CH$_2$CH$_3$)CH(CH(CH$_3$)$_2$)OH), 7.24-7.44 (m, 6H, 5×Bz-H+HNCH$_2$-Bz), 7.52 (s, 1H, —N=CH—N).

FABMS m/z (relative intensity): 397 ([M+H]⁺, 100), 323 (70). Accurate Mass (M+H): Actual: 397.2716, Measured: 393.2724.

Example 12

(3RS,4S)-4-(6-Benzylamino-9-isopropyl-9H-purin-2-ylamino)-2-methyl-hexan-3-ol

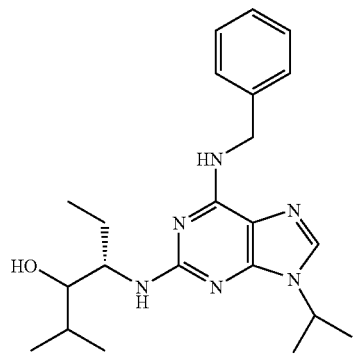

(3RS,4S)-2-Methyl-4-(trityl-amino)-hexan-3-ol

To a stirred suspension of CuBr.SMe₂ (1.37 g, 2.2 eq, 6.66 mmol) in ether (100 mL) under an argon atmosphere at −78° C., was added isopropyllithium (0.7 M in pentane, 17.29 mL, 4 eq, 12.1 mmol) dropwise and the solution allowed to warm to room temperature. The mixture was recooled to −70° C., to which was added a solution of (S)-2-(trityl-amino)-butyraldehyde (1 g, 1 eq, 3.03 mmol) in ether (25 mL) dropwise with stirring. The reaction mixture was stirred at this temperature for 1 h, then allowed to warm to −55° C. and stirred at this temperature for 3 h. To the reaction mixture was added a saturated aqueous solution of NH₄Cl (100 mL) and allowed to warm to room temperature over 16 h The reaction mixture was extracted with ether (2×200 mL), and the combined organic phase washed with brine (50 mL), dried (MgSO₄) and evaporated in vacuo. The residue was purified by silica gel column chromatography, eluted with hexane:ether (100:0→90:10) to afford the title compound as a colourless oil; Yield: 0.36 g (32%). (50% de 3R,4S, 50% de 3S,4S). ¹H-NMR (d₆-DMSO, 250 MHz): δ 0.44 (t, 3H, J=6.79 Hz, —NHCH(CH₂CH₃)CH(CH(CH₃)₂)OH), 0.52+0.76 (2×d, 6H, J=6.63 Hz, —NHCH(CH₂CH₃)CH(CH(CH₃)₂)OH), 0.80-1.15 (m, 2H, —NHCH(CH₂CH₃)CH(CH(CH₃)₂)OH), 1.70 (m, 1H, —NHCH(CH₂CH₃)CH(CH(CH₃)₂)OH), 2.10 (m, 1H, —NHCH(CH₂CH₃)CH(CH(CH₃)₂)OH), 2.76 (m, 1H, —NHCH(CH₂CH₃)CH(CH(CH₃)₂)OH), 2.99 (m, 1H, —NHCH(CH₂CH₃)CH(CH(CH₃)₂)OH), 4.55 (d, 1H, J=5.84 Hz, —NHCH(CH₂CH₃)CH(CH(CH₃)₂)OH), 7.17-7.46 (m, 15H, 3×Bz).

(3RS,4S)₄-Amino-2-methyl-hexan-3-ol

To a stirred solution of (3RS,4S)-2-methyl-4-(trityl-amino)-hexan-3-ol (0.36 g, 1 eq, 0.97 mmol) in DCM (20 mL) under an argon atmosphere at room temperature, was added trifluoroacetic acid (5 mL) dropwise, and the solution was stirred at this temperature for 1 h. The solvent was evaporated in vacuo, the residue was precipitated from ether (10 mL) with hexane (90 mL) with string to give a yellow oil. The solvent was decanted from the oil, and the oil was washed with hexane (20 mL) and dried in vacuo to afford the title compound as a light yellow oil; Yield: 0.13 g (100%). (50% de 3R,4S: 50% de 3S,4S), ¹H-NMR (d₆-DMSO, 250 MHz): δ 0.85-1.01 (m, 9H, NH₂CH(CH₂CH₃)CH(CH(CH₃)₂)OH), 1.44-1.76 (m, 2H, NH₂CH(CH₂CH₃)CH(CH(CH₃)₂)OH), 2.94 (m, 1H, NH₂CH(CH₂CH₃)CH(CH(CH₃)₂)OH), 3.17 (m, 1H, NH₂CH(CH₂CH₃)CH(CH(CH₃)₂)OH), 3.40 (m, 1H, NH₂CH(CH₂CH₃)CH(CH(CH₃)₂)OH), 7.54 (bs, 2H, NH₂CH(CH₂CH₃)CH(CH(CH₃)₂)OH).

(3RS,4S)-4-(6-Benzylamino-9-isopropyl-9H-purin-2-ylamino)-2-methyl-hexan-3-ol

To a stirred solution of benzyl-(2-fluoro-9-isopropyl-9H-purin-6-yl)-amine (40 mg, 1 eq, 0.14 mmol) in n-BuOH/DMSO (2.5 mL, 4:1) at room temperature under an argon atmosphere was added DIEA (0.24 mL, 4.9 eq, 1.38 mmol) followed by (3RS,4S)-4-amino-2-methyl-hexan-3-ol (39 mg, 2.12 eq, 0.30 mmol). The reaction mixture-was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×50 mL), and the combined organic phase was washed with brine (50 mL), dried (MgSO₄) and evaporated in vacuo. The residue was purified by gradient column chromatography on silica gel eluted with hexane:ether:MeOH (50:50:0→50:50:2) to afford the title compound as a white solid; Yield: 6.7 mg (12%). (50% de 45,3S: 50% de 4S,3R). ¹H-NMR (d-CDCl₃, 250 MHz): δ 0.95-1.04 (m, 9H, —NHCH(CH₂CH₃)CH(CH(CH₃)₂)OH), 1.57 (d, 6H, J=6.79 Hz, —CH(CH₃)₂), 1.62-1.88 (m, 4H, —NHCH(CH₂CH₃)CH(CH(CH₃)₂)OH), 3.26-3.32 (m, 1H, —NH CH(CH₂CH₃)CH(CH(CH₃)₂)OH), 3.87-4.00 (m, 1H, —NHCH(CH₂CH₃)CH(CH(CH₃)₂)OH), 4.57-4.70 (m, 1H, —CH(CH₃)₂), 4.76-4.90 (m, 2H, —HNCH₂-Bz), 5.25-5.55 (m, 1H NHCH(CH₂CH₃)CH(CH(CH₃)₂)OH), 7.26-7.45 (m, 6H, 5×Bz-H+HNCH₂-Bz), 7.53 (s, 1H, —N═CH—N). FABMS m/z (relative intensity): 397 ([M+H]⁺, 95), 385 (20), 323 (100). Accurate Mass (M+H): Actual: 397.2716, Measured: 393.2724.

Example 13

(3RS,4R)-4-(6-Benzylamino-9-isopropyl-9H-purin-2-ylamino)-2,2-dimethyl-hexan-3-ol

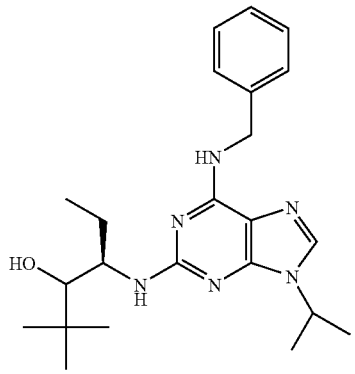

(3RS,4R)-2,2-Dimethyl-4-(trityl-amino)-hexan-3-ol

To a stirred suspension of CuBr.SMe₂ (1.37 g, 2.2 eq, 6.66 mmol) in ether (100 mL) under an argon atmosphere at −78°

C., was added tert-butyllithium (1.5 M in pentane, 8.0 mL, 4 eq, 12.0 mmol) dropwise and the solution allowed to warm to room temperature. The mixture was recooled to −55° C., to which was added a solution of (R)-2-(trityl-amino)-butyraldehyde (1 g, 1 eq, 3.03 mmol) in ether (25 mL) dropwise with stirring, and stirred at this temperature for 3 h. To the reaction mixture was added a saturated aqueous solution of $NH_4Cl$ (100 mL) and allowed to warm to room temperature over 16 h. The reaction mixture was extracted with ether (2×200 mL), and the combined organic phase washed with brine (50 mL), dried ($MgSO_4$) and evaporated in vacuo. The residue was purified by silica gel gradient column chromatography, eluted with hexane:ether (100:0→90:10) to afford the title compound as a light yellow oil; Yield: 0.57 g (49%). (55% de 3S,4R: 45% de 3R,4R) $^1$H-NMR ($d_6$-DMSO, 250 MHz): δ 0.36+0.86 (2×t 3H, J=7.42 Hz, —NHCH(CH$_2$CH$_3$)CH(C(CH$_3$)$_3$)OH), 0.57+0.71 (2×s, 9H, —NHCH(CH$_2$CH$_3$)CH(C(CH$_3$)$_3$)OH), 1.38-1.52 (m, 2H, —NHCH(CH$_2$CH$_3$)CH(C(CH$_3$)$_3$)OH), 1.99 (m, 1H, —NHCH(CH$_2$CH$_3$)CH(C(CH$_3$)$_3$)OH), 2.27 (m, 1H, —NHCH(CH$_2$CH$_3$)CH(C(CH$_3$)$_3$)OH), 2.95 (m, 1H, —NHCH(CH$_2$CH$_3$)CH(C(CH$_3$)$_3$)OH), 4.22+4.77 (2×d, 1H, J=4.42+5.21 Hz, —NHCH(CH$_2$CH$_3$)CH(C(CH$_3$)$_3$)OH), 7.14-7.52 (m, 15H, 3×Bz).

(3RS,4R)-4-Amino-2,2-dimethyl-hexan-3-ol

To a stirred solution of (3RS,4R)-2,2-dimethyl-4-(trityl-amino)-hexan-3-ol (0.57 g, 1 eq, 1.47 mmol) in DCM (10 mL) under an argon atmosphere at room temperature, was added trifluoroacetic acid (5 mL) dropwise, and the solution was stirred at this temperature for 1 h. The solvent was evaporated in vacuo, the residue was precipitated from ether (3 mL) with hexane (20 mL) with sting to give a yellow oil. The solvent was decanted from the oil, and the oil was washed with hexane (20 mL) and dried in vacuo to afford the title compound as a light yellow oil; Yield: 0.21 g (100%). (55% de 3S,4R: 45% de 3R,4R) $^1$H-NMR ($d_6$-DMSO, 250 MHz): δ 0.84-0.99 (m, 3H, NH$_2$CH(CH$_2$CH$_3$)CH(C(CH$_3$)$_3$)OH), 1.25-1.29 (m, 9H, NH$_2$CH(CH$_2$CH$_3$)CH(C(CH$_3$)$_3$)OH), 1.20-1.72 (m, 2H, NH$_2$CH(CH$_2$CH$_3$)CH(C(CH$_3$)$_3$)OH), 3.14 (m, 1H, NH$_2$CH(CH$_2$CH$_3$)CH(C(CH$_3$)$_3$)OH), 3.39 (m, 1H, NH$_2$CH(CH$_2$CH$_3$)CH(C(CH$_3$)$_3$)OH), 3.65 (m, 1H, NH$_2$CH(CH$_2$CH$_3$)CH(C(CH$_3$)$_3$)OH), 7.43, 7.77+8.54 (3×bs, 2H, NH$_2$CH(CH$_2$CH$_3$)CH(CH(CH$_3$)$_2$)OH).

(3RS,4R)-4-(6-Benzylamino-9-isopropyl-9H-purin-2-ylamino)-2,2-dimethyl-hexan-3-ol To a stirred solution of benzyl-(2-fluoro-9-isopropyl-9H-purin-6-yl)-amine (40 mg, 1 eq, 0.14 mmol) in n-BuOH/DMSO (5 mL, 4:1) at room temperature under an argon atmosphere was added DIEA (0.12 mL, 4.9 eq, 0.69 mmol) followed by (3RS,4R)-4-amino-2,2-dimethyl-hexan-3-ol (69 mg, 3.4 eq, 0.48 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×50 mL), and the combined organic phase was washed with brine (50 mL), dried ($MgSO_4$) and evaporated in vacuo. The residue was purified by gradient column chromatography on silica gel eluted with hexane:ether:MeOH (50:50:0→50:50:2) to afford the title compound as a white solid; Yield: 13 mg (23%).(55% de 4R,3S: 45% de 4R,3R).

$^1$H-NMR (d-CDCl$_3$, 250 MHz): δ 1.00-1.04 (m, 12H, —NHCH(CH$_2$CH$_3$)CH(C(CH$_3$)$_3$)OH), 1.56+1.58 (2×d, 6H, J=6.63+6.79 Hz, —CH(CH$_3$)$_2$), 1.63-1.87 (m, 2H, —NHCH(CH$_2$CH$_3$)CH(C(CH$_3$)$_3$)OH), 3.57 (d, 1H, J=1.42 Hz, —NHCH(CH$_2$CH$_3$) CH(C(CH$_3$)$_3$)OH), 3.73-3.87 (m, 1H, —NHCH(CH$_2$CH$_3$)CH(C(CH$_3$)$_3$)OH), 4.57-4.70 (m, 1H, —CH(CH$_3$)$_2$), 4.77-4.86 (m, 2H, —HNCH$_2$-Bz), 5.22-5.36+5.93-6.09 (2×m, 1H, —NHCH(CH$_2$CH$_3$)CH(C(CH$_3$)$_3$)OH), 7.25-7.44 (m, 6H, 5×Bz-H+HNCH$_2$-Bz), 7.53 (s, 1H, —N=CH—N). FABMS m/z (relative intensity): 411 ([M+H]$^+$, 90), 323 (100). Accurate Mass (M+H): Actual: 411.2872, Measured: 411.2860.

Example 14

(3RS,4S)-4-(6-Benzylamino-9-isopropyl-9H-purin-2-ylamino)-2,2-dimethyl-hexan-3-ol

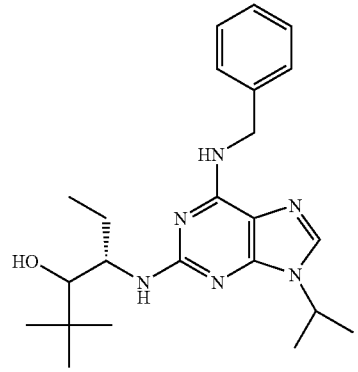

(3RS,4S)-2,2-Dimethyl-4-(trityl-amino)-hexan-3-ol

To a stirred suspension of CuBr.SMe$_2$ (1.37 g, 2.2 eq, 6.66 mmol) in ether (100 mL) under an argon atmosphere at −78° C., was added tert-butyl lithium (1.5 M in pentane, 8.0 mL, 4 eq, 12.0 mmol) dropwise and the solution allowed to warm to room temperature. The mixture was recooled to −55° C., to which was added a solution of (S)-2-(trityl-amino)-butyraldehyde (1 g, 1 eq, 3.03 mmol) in ether (25 mL) dropwise with stirring, and stirred at this temperature for 3 h. To the reaction mixture was added a saturated aqueous solution of $NH_4Cl$ (100 mL) and allowed to warm to room temperature over 16 h. The reaction mixture was extracted with ether (2×200 mL), and the combined organic phase washed with brine (50 mL), dried ($MgSO_4$) and evaporated in vacuo. The residue was purified by silica gel column chromatography, eluted with hexane:ether (100:0→90:10) to afford the title compound as a light yellow oil; Yield: 0.47 g (40%). (53% de 3R,4S: 47% de 3S,4S) $^1$H-NMR ($d_6$-DMSO, 250 MHz): δ 0.37+0.87 (2×t, 3H, J=7.46 Hz, —NHCH(CH$_2$CH$_3$)CH(C(CH$_3$)$_3$)OH), 0.58+0.71 (2×s, 9H, —NHCH(CH$_2$CH$_3$)CH(C(CH$_3$)$_3$)OH), 1.38-1.52 (m, 2H, —NHCH(CH$_2$CH$_3$)CH(C(CH$_3$)$_3$)OH), 2.00 (m, 1H, —NHCH(CH$_2$CH$_3$)CH(C(CH$_3$)$_3$)OH), 2.28 (m, 1H, —NHCH(CH$_2$CH$_3$)CH(C(CH$_3$)$_3$)OH), 2.95 (m, 1H, —NHCH(CH$_2$CH$_3$)CH(C(CH$_3$)$_3$)OH), 4.24+4.79 (2×d, 1H, J=5.21+6.16 Hz, —NHCH(CH$_2$CH$_3$)CH(C(CH$_3$)$_3$)OH), 7.15-7.53 (m, 15H, 3×Bz).

(3RS,4S)-4-Amino-2,2-dimethyl-hexan-3-ol

To a stirred solution of (3RS,4S)-2,2-dimethyl-4-(tritylamino)-hexan-3-ol (0.47 g, 1 eq, 1.21 mmol) in DCM (10 mL) under an argon atmosphere at room temperature, was added trifluoroacetic acid (5 mL) dropwise, and the solution was stirred at this temperature for 1 h. The solvent was evaporated in vacuo, the residue was precipitated from ether (3 mL) with hexane (20 mL) with stirring to give a yellow oil. The solvent was decanted from the oil, and the oil was washed with hexane (20 mL) and dried in vacuo to afford the title compound as a light yellow oil; Yield: 0.18 g (99%). (53% de 3R,4S: 47% de 3S,4S). $^1$H-NMR (d$_6$-DMSO, 250 MHz): δ 0.86-0.99 (m, 3H, NH$_2$CH(CH$_2$CH$_3$)CH(C(CH$_3$)$_3$)OH), 1.25-1.30 (m, 9H, NH$_2$CH(CH$_2$CH$_3$)CH(C(CH$_3$)OH), 1.20-1.67 (m, 2H, NH$_2$CH(CH$_2$CH$_3$)CH(C(CH$_3$)$_3$)OH), 3.14 (m, 1H, NH$_2$CH(CH$_2$CH$_3$)CH(C(CH$_3$)$_3$)OH), 3.38 (m, 1H, NH$_2$CH(CH$_2$CH$_3$)CH(C(CH$_3$)$_3$)OH), 3.64 (m, 1H, NH$_2$CH(CH$_2$CH$_3$)CH(C(CH$_3$)$_3$)OH), 7.41, 7.73+8.44 (3×bs, 2H, NH$_2$CH(CH$_2$CH$_3$)CH(CH(CH$_3$)$_2$)OH).

(3RS,4S)-4-(6-Benzylamino-9-isopropyl-9H-purin-2-ylamino)-2,2-dimethyl-hexan-3-ol To a stirred solution of benzyl-(2-fluoro-9-isopropyl-9H-purin-6-yl)-amine (40 mg, 1 eq, 0,14 mmol) in n-BuOH/DMSO (5 mL, 4:1) at room temperature under an argon atmosphere was added DIEA (0.12 mL, 4.9 eq, 0.69 mmol) followed by (3RS,4S)-4-amino-2,2-dimethyl-hexan-3-ol (57 mg, 2.8 eq, 0.39 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×50 mL), and the combined organic phase was washed with brine (50 mL), dried (MgSO$_4$) and evaporated in vacuo. The residue was purified by gradient column chromatography on silica gel eluted with hexane:ether:MeOH (50:50:0→50:50:2) to afford the title compound as a white solid; Yield: 7.2 mg (13%). (53% de 4S,3R: 47% de 4S,3S). $^1$H-NMR (d-CDCl$_3$, 250 MHz): δ 0.99-1.04 (m, 12H, —NHCH(CH$_2$CH$_3$)CH(C(CH$_3$)$_3$)OH), 1.56+1.58 (2×d, 6H, J=6.63+6.79 Hz, —CH(CH$_3$)$_2$), 1.64-1.87 (m, 2H, —NHCH(CH$_2$CH$_3$)CH(C(CH$_3$)$_3$)OH), 3.57 (d, 1H, J=1.42 Hz, —NHCH(CH$_2$CH$_3$)CH(C(CH$_3$)$_3$)OH), 3.73-3.86 (m, 1H, —NHCH(CH$_2$CH$_3$)CH(C(CH$_3$)$_3$)OH), 4.57-4.69 (m, 1H, —CH(CH$_3$)$_2$), 4.78-4.86 (m, 2H, —HNCH$_2$-Bz), 5.22-5.34+5.95-6.08 (2×m, 1H, —NHCH(CH$_2$CH$_3$)CH(C(CH$_3$)$_3$)OH), 7.26-7.44 (m, 6H, 5×Bz-H+HNCH$_2$-Bz), 7.53 (s, 1H, —N═CH—N). FABMS m/z (relative intensity): 411 ([M+H]$^+$, 85), 323 (100). Accurate Mass (N+H): Actual: 411.2872, Measured: 411.2860.

Example 15

(R)-3-(6-Benzylamino-9-isopropyl-9H-purin-2-ylamino 2-methyl-pentan-2-ol

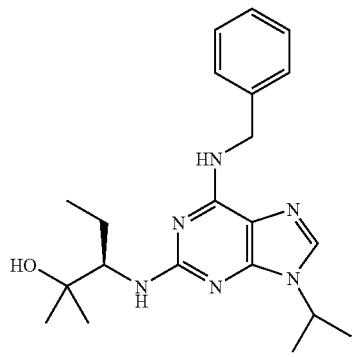

(2S,3R)-3-(Trityl-amino)-pentan-2-one

To a stirred solution of DMSO (2.19 mL, 2.8 eq, 30.86 mmol) in DCM (30 mL) under an argon atmosphere at 45° C., was added oxalyl chloride (2 M in DCM, 7.69 mL, 1.4 eq, 15.38 mmol) dropwise. The reaction mixture was stirred at −45° C. for 1 h, after which time a solution (2S,3R)-3-(tritylamino)-pentan-2-ol (3.81 g, 1 eq, 11.04 mmol) in DCM (20 mL) was added dropwise with stirring. The reaction mixture was stirred at this temperature for 4 h, when TLC (hexane:ether; 80:20) indicated &hat the reaction had gone to completion. To the reaction mixture was added N-ethylpiperidine (7.54 mL, 5 eq, 54.88 mmol), and the solution allowed to warm to room temperature over 16 h. The reaction mixture was diluted with more DCM (50 mL) and washed with water (200 mL). The aqueous phase was extracted with DCM (2×50 mL), and the combined organic phase washed with brine (50 mL), dried (MgSO$_4$) and evaporated in vacuo. The residue was dissolved in ether (100 mL), the solid precipitate removed by filtration and the filtrate was evaporated in vacuo. The residue was dissolved in hexane (50 mL), the solid precipitate removed by filtration and the filtrate was evaporated in vacuo to afford the title compound as a light yellow oil; Yield: 3.78 g (100%). (80% de 2S,3R: 20% de 2R,3R). $^1$H-NMR (d$_6$-DMSO, 250 MHz): δ 0.73 (t, 3H, J=7.35 Hz, —NHCH(CH$_2$CH$_3$)C(CH$_3$)O), 1.47-1.60 (m, 5H, —NHCH(CH$_2$CH$_3$)C(CH$_3$)O), 3.12 (d, 1H, J=8.38 Hz, —NHCH(CH$_2$CH$_3$)C(CH$_3$)O), 3.32 (m, 1H, —NHCH(CH$_2$CH$_3$)C(CH$_3$)O), 7.16-7.49 (m, 15H, 3×Bz).

(R)-2-Methyl-3-(trityl-amino)-pentan-2-ol

To a stirred solution of (2S,3R)-3-(trityl-amino)-pentan-2-one (0.87 g, 1 eq, 2.54 mmol) in ether (100 mL) under an argon atmosphere at room temperature, was added methylmagnesium iodide (3 M in ether, 2.54 mL, 3 eq, 7.62 mmol) dropwise. The solution was placed in a preheated oil bath at 45° C. and refluxed at this temperature for 16 h. The mixture was re-cooled to 0° C., H$_2$O (100 mL) added, the solution filtered through Celite, and the Celite washed with more ether (50 mL). The combined organic phase was separated, the aqueous phase was extracted with ether (2×50 mL), and the combined organic phase washed with brine (50 mL), dried (MgSO$_4$) and evaporated in vacuo. The residue was purified by silica gel column chromatography, eluted with hexane: ether (100:0→90:10) to afford the title compound as a light yellow oil; Yield: 0.21 g (23%). $^1$H-NMR (d$_6$-DMSO, 250 MHz): δ 0.26 (t, J=7.42 Hz, —NHCH(CH$_2$CH$_3$)CH(CH$_3$)OH), 1.00+1.25 (2×s, 6H, —NHCH(CH$_2$CH$_3$)C(CH$_3$)$_2$OH), 0.72-1.43 (m, 2H, —NHCH(C$_2$CH$_3$)C(CH$_3$)$_2$OH), 1.84 (m, 1H, —NHCH(CH$_2$CH$_3$)C(CH$_3$)$_2$ OH), 2.90 (m, 1H, —NHCH(CH$_2$CH$_3$)C(CH$_3$)$_2$OH), 4.32 (s, 1H, —NHCH(CH$_2$CH$_3$)C(CH$_3$)$_2$OH), 7.17-7.46 (m, 15H, 3×Bz).

(R)-3-Amino-2-methyl-pentan-2-ol

To a stirred solution of (R)-2-methyl-3-(trityl-amino)-pentan-2-ol (0.21 g, 1 eq, 0.60 mmol) in DCM (5 mL) under an argon atmosphere at room temperature, was added trifluoroacetic acid (2.5 mL) dropwise, and the solution was stirred at this temperature for 1 h. The solvent was evaporated in vacuo and the residue was precipitated from ether (15 mL) with hexane (300 mL) with stirring to give a yellow oil. The solvent was decanted from the oil, and the oil was washed with hexane (30 mL) and dried in vacuo to afford the title compound as a light yellow oil; Yield: 0.07 g (100%). $^1$H-NMR (d$_6$-DMSO, 250 MHz); δ 0.97 (t, 3H, J=7.42 Hz, NH$_2$CH(CH$_2$CH$_3$)C(CH$_3$)$_2$OH), 1.06+1.19 (2×s, 6H, NH$_2$CH(CH$_2$CH$_3$)C(CH$_3$)$_2$OH), 1.28-1.71 (m, 2H, NH$_2$CH(CH$_2$CH$_3$)C(CH$_3$)$_2$OH), 2.72 (m, 1H, NH$_2$CH(CH$_2$CH$_3$)C(CH$_3$)$_2$OH), 5.21 (s, 1H, NH$_2$CH(CH$_2$CH$_3$)C(CH$_3$)$_2$OH), 7.63 (bs, 2H, NH$_2$CH(CH$_2$CH$_3$)C(CH$_3$)$_2$OH).

(R)-3-(6-Benzylamino-9-isopropyl-9H-purin-2-ylamino)-2-methyl-pentan-2-ol

To a stirred solution of benzyl-(2-fluoro-9-isopropyl-9H-purin-6-yl)-amine (20 mg, 1 eq, 0.07 mmol) in n-BuOH/DMSO (1.25 mL, 4:1) at room temperature under an argon atmosphere was added DIEA (0.25 mL, 20.4 eq, 1.43 mmol) followed by (R)-3-amino-2-methyl-pentan-2-ol (22 mg, 2.68 eq, 0.19 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water (1:1, 100 mL), the aqueous phase was extracted with more EtOAc (2×50 mL), and the combined organic phase was washed with brine (50 mL), dried (MgSO$_4$) and evaporated in vacuo. The residue was purified by gradient column chromatography on silica gel eluted with hexane:ether:MeOH (50:50:0→50:50:2) to afford the title compound as a white solid; Yield: 4.2 mg (16%). $^1$H-NMR (d-CDCl$_3$, 250 MHz): δ 1.01 (t, 3H, J=7.50 Hz, —NHCH(CH$_2$CH$_3$)C(CH$_3$)$_2$OH), 1.23+1.30 (2×s, 6H, —NHCH(CH$_2$CH$_3$)C(CH$_3$)$_2$OH), 1.57 (d, 6H, J=6.79 Hz, —CH(CH$_3$)$_2$), 1.68-1.89 (m, 2H, —NHCH(CH$_2$CH$_3$)C(CH$_3$)$_2$OH), 3.69-3.86 (m, 1H, —NHCH(CH$_2$CH$_3$)C(CH$_3$)$_2$OH), 4.58-4.74 (m, 1H, —CH(CH$_3$)$_2$), 4.75-4.94 (m, 2H, —HNCH$_2$-Bz), 7.22-7.45 (m, 6H, 5×Bz-H+HNCH$_2$-Bz), 7.57 (s, 1H, —N=CH—N). FABMS m/z (relative intensity): 383 ([M+H]$^+$, 75), 323 (60), 308 (20), 246 (20), 192 (60), 176 (100), 165 (40). Accurate Mass (M+H): Actual: 383.2559, Measured: 383.2544.

Example 16

(S)-3-(6-Benzylamino-9-isopropyl-9H-purin-2-ylamino)-2 methyl-pentan-2-ol

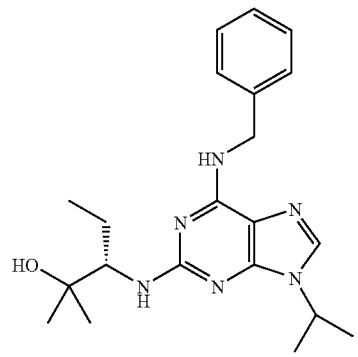

(2R 3S)-3-(Trityl-amino)-pentan-2-one

To a stirred solution of DMSO (1.95 mL, 2.8 eq, 27.48 mmol) in DCM (30 mL) under an argon atmosphere at −45° C., was added oxalyl chloride (2 M in DCM, 6.85 mL, 1.4 eq, 13.70 mmol) dropwise. The reaction mixture was stirred at −45° C. for 1 h, after which time a solution (2R,3S)-3-(trityl-amino)-pentan-2-ol (3.39 g, 1 eq, 9.83 mmol) in DCM (20 mL) was added dropwise with stirring. The reaction mixture was stirred at this temperature for 4 h, when TLC (hexane:ether; 80:20) indicated that the reaction had gone to completion. To the reaction mixture was added N-ethylpiperidine (6.71 mL, S eq, 48.84 mmol), and the solution allowed to warm to room temperature over 16 h. The reaction mixture was diluted with more DCM (50 mL) and washed with water (200 mL). The aqueous phase was extracted with DCM (2×50 mL), and the combined organic phase washed with brine (50 mL), dried (MgSO$_4$) and evaporated in vacuo. The residue was dissolved in ether (100 mL), the solid precipitate removed by filtration and the filtrate was evaporated in vacuo. The residue was dissolved in hexane (50 mL), the solid precipitate removed by filtration and the filtrate was evaporated in vacuo to afford the title compound as a light yellow oil; Yield: 3.15 g (93%). (80% de 2R,3S: 20% de 2S,3S). $^1$H-NMR (d$_6$-DMSO, 250 MHz): δ 0.73 (t, 3H, J=7.50 Hz, —NHCH(CH$_2$CH$_3$)C(CH$_3$)O), 1.45-1.62 (m, 5H, —NHCH(CH$_2$CH$_3$)C(CH$_3$)O), 3.12 (d, 1H, J=8.53 Hz, —NHCH(CH$_2$CH$_3$)C(CH$_3$)O), 3.31 (m, 1H, —NHCH(CH$_2$CH$_3$)C(CH$_3$)O), 7.13-7.45 (m, 15H, 3×Bz).

(S)-2-Methyl-3-(trityl-amino)-pentan-2-ol

To a stirred solution of (2R,3S)-3-(trityl-amino)pentan-2-one (0.59 g, 1 eq, 1.72 mmol) in ether (100 mL) under an argon atmosphere at room temperature, was added methylmagnesium iodide (3 M in ether, 1.72 mL, 3 eq, 5.16 mmol) dropwise. The solution was placed in a preheated oil bath at 45° C. and refluxed at this temperature for 16 h. The mixture was re-cooled to 0° C., H$_2$O (100 mL) added, the solution filtered through Celite, and the Celite washed with more ether (50 mL). The combined organic phase was separated, the aqueous phase was extracted with ether (2×50 mL), and the combined organic phase washed with brine (50 mL) dried (MgSO$_4$)-and evaporated in vacuo. The residue was purified by silica gel column chromatography, eluted with hexane: ether (100:0→90:10) to afford the title compound as a light yellow oil; Yield: 0.10 g (16%). $^1$H-NMR (d$_6$-DMSO, 250 MHz): δ 0.27 (t, J=7.10 Hz, —NHCH(CH$_2$CH$_3$)CH(CH$_3$)OH), 0.99+1.25 (2×s, 6H, —NHCH(CH$_2$CH$_3$)C(CH$_3$)$_2$OH), 0.75-1.42 (m, 2H, —NHCH(CH$_2$CH$_3$)C(CH$_3$)$_2$OH), 1.88 (m, 1H, —NHCH(CH$_2$CH$_3$)C(CH$_3$)$_2$OH), 2.92 (m, 1H, —NHCH(CH$_2$CH$_3$)C(CH$_3$)$_2$OH), 4.32 (s, 1H, —NHCH(CH$_2$CH$_3$)C(CH$_3$)$_2$OH), 7.18-7.46 (m, 15H, 3×Bz).

(S)-3-Amino-2-methyl-pentan-2-ol

To a stirred solution of (S)-2-methyl-3-trityl-amino)-pentan-2-ol (0.38 g, 1 eq, 1.06 mmol) in DCM (5 mL) under an argon atmosphere at room temperature, was added trifluoroacetic acid (2.5 mL) dropwise, and the solution was stirred at this temperature for 1 h. The solvent was evaporated in vacuo and the residue was precipitated from ether (15 mL) with hexane (300 mL) with string to give a yellow oil. The solvent was decanted from the oil, and the oil was washed with hexane (30 mL) and dried in vacuo to afford the title compound as a light yellow oil; Yield: 0.12 g (99%). $^1$H-NMR (d$_6$-DMSO, 250 MHz): δ 0.97 (t, 3H, J=7.42 Hz, NH$_2$CH(CH$_2$CH$_3$)C(CH$_3$)$_2$OH), 1.07+1.19 (2×s, 6H, NH$_2$CH(CH$_2$CH$_3$)C(CH$_3$)$_2$OH), 1.28-1.61 (m, 2H, NH$_2$CH(CH$_2$CH$_3$)C(CH$_3$)$_2$OH), 2.72 (m, 1H, NH$_2$CH(CH$_2$CH$_3$)C(CH$_3$)$_2$OH), 5.21 (s, 1H, NH$_2$CH(CH$_2$CH$_3$)C(CH$_3$)$_2$OH), 7.63 (bs, 2H, NH$_2$CH(CH$_2$CH$_3$)C(CH$_3$)$_2$OH).

(S)-3-(6-Benzylamino-9-isopropyl-9H-purin-2-ylamino)-2-methyl-pentan-2-ol

To a stirred solution of benzyl-2-fluoro-9-isopropyl-9H-purin-6-yl)-amine (30 mg, 1 eq, 0.11 mmol) in n-BuOH/DMSO (1.25 mL, 4:1) at room temperature under an argon atmosphere was added DIEA (0.25 mL, 13.65 eq, 1.43 mmol) followed by (S)-3-amino-2-methyl-pentan-2-ol (40 mg, 3.25 eq, 0.34 mmol). The reaction mixture was placed in a preheated oil bath at 140° C. and stirred at this temperature for 72 h. The reaction mixture was allowed to cool to room temperature and the solvent was evaporated in vacuo. The residue was partitioned between EtOAc (50 mL) and brine/water(1:1,100 mL), the aqueous phase was extracted with more EtOAc-(2× 50 mL), and the combined organic phase was washed with brine (50 mL), dried (MgSO$_4$) and evaporated in vacuo. The residue was purified by gradient column chromatography on silica gel eluted with hexane:ether:MeOH (50:50:0→50:50: 2) to afford the title compound as a white solid; Yield: 7.3 mg (18%). $^1$H-NMR (d-CDCl$_3$, 250 MHz): δ 1.01 (t, 3H, J=7.42 Hz, —NHCH(CH$_2$CH$_3$)C(CH$_3$)$_2$OH), 1.23+1.31 (2×s, 6H, —NHCH(CH$_2$CH$_3$)C(CH$_3$)$_2$OH), 1.58 (d, 6H, J=6.79 Hz, —CH(CH$_3$)$_2$), 1.69-2.00 (m, 2H, —NHCH(CH$_2$CH$_3$)C(CH$_3$)$_2$OH), 3.70-3.87 (m, 1H, —NHCH(CH$_2$CH$_3$)C(CH$_3$)$_2$OH), 4.59-4.73 (m, 1H, —CH(CH$_3$)$_2$), 4.74-4.97 (m, 2H, —HNCH$_2$-Bz), 7.23-7.45 (m, 6H, 5×Bz-H+HNCH$_2$-Bz), 7.56 (s, 1H, —N=CH—N). FABMS m/z (relative intensity): 383 ([M+H]$^+$, 85), 323 (100). Accurate Mass (M+H): Actual: 383.2559, Measured: 383.2544.

The biological activity of the compounds of the invention was demonstrated by measuring the CDK inhibition by virtue of an assay-based screen, and/or by a cytotoxicity assay using one or more cell lines. The results are shown below in Tables 1 and 2.

Example 17

Kinase Specificity of Selected Compound

Selected compounds from the above examples were investigated for their CDK2/cyclin E, CDK1/cyclin B, CDK4/cyclin D1 and CDK7/cyclin H activity.

Assays for CDK2/cyclin E kinase, CDK1/cyclin B and CDK4/cyclin D1 may be carried out by monitoring phosphorylation of GST-Rb in an appropriate system. Thus, GST-Rb phosphorylation, induced by CDK2/Cyclin E, CDK1/cyclin B or CDK4/cyclin D1 is determined by incorporation of radiolabelled phosphate in GST-Rb(772-928) using radiolabelled ATP in 96-well format in vitro kinase assay. The phosphorylation reaction mixture (total volume 40 µl) consisted of 50 mM HEPES pH 7.4, 20 mM MgCl$_2$, 5 mM EGTA, 2 mM DTT, 20 mM β-glycerophosphate, 2 mM NaF, 1 mM Na$_3$VO$_4$, Protease Inhibitors Cocktail (Sigma, see above), BSA 0.5 mg/ml, 1 µg purified enzyme complex, 10 µl of GST-Rb-Sepharose-beads, 100 µM ATP, 0.2 µCi $^{32}$P-ATP. The reaction is carried out for 30 min at 30° C. at constant shaking. At the end of this period 100 µl of 50 mM HEPES, pH 7.4 and 1 mM ATP is added to each well and the total volume transferred onto GFC filtered plate. The plate is washed 5 times with 200 µl of 50 mM HEPES, pH 7.4 and 1 mM ATP. To each well was added 50 µl scintillant liquid and the radioactivity of the samples is measured on Scintilation counter (Topcount, HP). The IC50 values of different peptides were calculated using GraFit software.

For use in said assay CDK2 may be obtained from available sources or produced by recombinant methods as described His-tagged CDK2/Cyclin E and CDK1/Cyclin B may be co-expressed in Sf9 insect cells infected with the appropriate baculovirus constructs. The cells are harvested two days after infection by low speed centrifugation and the proteins purified from the insect cell pellets by Metal-chelate chromatography. Briefly, the insect cell pellet is lysed in Buffer A (10 mM Tris-HCl, pH 8.0, 150 mM NaCl, 0.02% NP40 and 5 mM, β-marcaptoethanol, 1 mM NaF. 1 mM Na$_3$VO$_4$ and Protease Inhibitors Coctail (Sigma) containing AEBSF, pepstatin A, E 64, bestatin, leupeptin) by sonication. The soluble fraction is cleared by centrifugation and loaded onto Ni-NTA-Agarose (Quiagen). Non bound proteins were washed off with 300 mM NaCl, 5-15 mM Imidazole in Buffer A and the bound proteins eluted with 250 mM Imidazole in Buffer A. The purified proteins are extensively dialyzed against Storage buffer (20 mM HEPES pH 7.4, 50 mM NaCl, 2 mM DTT, 1 mM EDTA, 1 mM EGTA, 0.02% NP40, 10% v/v Glycerol) aliquoted and stored at −70° C. PKC-α—6×His may be purified the same way but using different buffers—50 mM NaH2PO4, pH 8.0 and 0.05% Triton X-100 instead of Tris and NP40 respectively.

ERK-2 kinase activity was measured by the incorporation of radioactive phosphate into myelin basic protein (MBP), catalysed by purified mouse ERK-2 (Upstate Biotechnologies). The reaction mixture (total volume 50 µL) consisted of 20 mM MOPS, pH 7.0,25 mM β-glycerophosphate, 5 mM EGTA, 1 mM DTT, 1 mM Na$_3$VO$_4$, 10 mM MgCl$_2$, 100 µM ATP, 0.2 µCi [γ-$^{32}$P]-ATP.

PKA kinase activity was measured by incorporation of radioactive phosphate into the peptide Kemptide (Fluka Biochemika Cat 60645), catalysed by cyclic AMP-dependent kinase (PKA) catalytic subunit (Calbiochem Cat 539487). The reaction mixture (total volume 50 µl) consisted of 20 mM MOPS, pH 7.2, 25 mM β-glycerophosphate, 5 mM EGTA, 1 mM DTT, 1 mM Na$_3$VO$_4$, 10 mM MgCl$_2$, 100 µM ATP, 0.2 µCi [γ-$^{32}$P]-ATP.

Example 18

Anti-Proliferative Effect of Selected Compounds

Selected compounds from the above examples were subjected to a standard cellular proliferation assay using seven different human tumour cell lines: A2780, A278CisF, CH1, CH1DoxR, HCT116, HT29 and KM12. Standard 72-h MTT (thiazolyl blue; 3-[4,5-dimethylthiazol-2-yl]-2,5-diphenyltetrazolium bromide) assays were performed (Haselsberger, K.; Peterson, D. C.; Thomas, D. G.; Darling, J. L. Anti Cancer Drugs 1996, 7, 331-8; Loveland, B. E.; Johns, T. G.; Mackay, I. R; Vaillant, F.; Wang, Z. X; Hertzog, P. J. Biochemistry International 1992, 27, 501-10). Human tumour cell lines were obtained from the ATCC (American Type Culture Collection, 10801 University Boulevard, Manessas, Va. 20110-2209, USA). The results are shown in Table 1, together with the average $IC_{50}$ over the seven different cell lines.

It has been shown that the main in vivo metabolic deactivation pathway of the experimental anti-proliferative CDK-inhibitory agent Roscovitine (refer PCT Intl. Patent Appl. WO 97/20842) comprises oxidation of the carbinol group to a carboxyl group and subsequent excretion of this metabolite [Nutley, B. P., Raynaud, F. I., Wilson, S. C., Fischer, P., McClue, S., Goddard, P. M., Jarman, M., Lane, D., and Workman, P. *Clin. Cancer Res.* 2000, 6 Suppl. (proc. 11$^{th}$ AACR-NCI-EORTC Intl. Conf. #318)]. Authentic synthetic material (refer Example 10), identical with this metabolite, shows reduced biological activity in vitro. Thus Roscovitine and the carboxyl derivative inhibit CDK2/cyclin E activity with $IC_{50}$ values of 0.08 and 0.24 µM, respectively. Similarly, the average anti-proliferative $IC_{50}$ values in a representative panel of human transformed tumour cell lines for Roscovitine and the carboxyl derivative were ca. 10 and >50 µM, respectively.

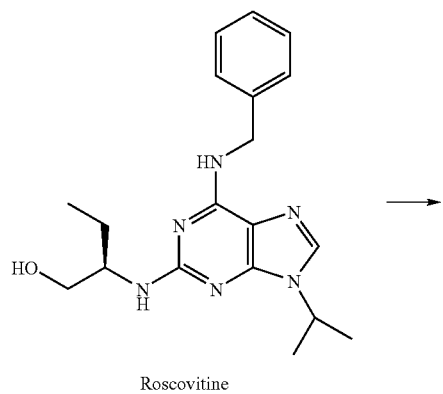

Roscovitine

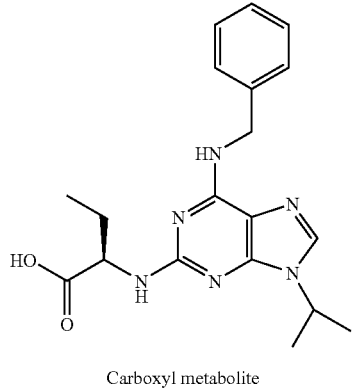

Carboxyl metabolite

In an attempt to prevent metabolic deactivation, analogues of Roscovitine containing modified purine C-2 substituents were therefore envisaged. Thus replacement of the primary alcohol function with secondary alcohols in 2,6,9-trisubstituted purines such as Roscovitine should prevent metabolic alcohol-carboxyl conversion. Pharmacokinetic analysis of e.g. the title compounds in Examples 1 & 2 showed that similar blood levels (AUC: area under the curve) and improved half-lives ($t_{1/2}$) could indeed be achieved when these compounds were administered to mice under similar conditions as Roscovitine. Results are given in Table 1. Comparative values for Roscovotine were: AUC=75454 nh-h/mL, $t_{1/2}$=2.7 h. Pharmacokinetic analysis was carried out as described previously [Raynaud, F. I., Nutley, B. P., Goddard, P., Fischer, P. M., Marriage, H., Lane, D., and Workman, P. *Clin. Cancer Res.* 1999, 5 Suppl. (Proc. 10$^{th}$ AACR-NCI-EORTC Intl. Conf. #541)]. Additional examples of compounds possessing modifications that prevent carbinol-carboxyl oxidation while maintaining biological activity at a similar level as Roscovitine are also shown in Table 1.

A further aim was to provide bioactive analogues of Roscovitine, which would possess improved aqueous solubility for the purposes of parenteral administration. It was found that replacement of the benzyl group with pyridylmethyl groups, particularly the pyrid-2-ylmethyl group, fulfilled this criterion (refer Table 1). The pyridylmethyl compounds have considerably lower calculated n-octanol/water partition coefficients (ClogP 2.22 compared to 3.7 for Roscovitine).

Various modifications and variations of the described methods of the invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the relevant fields are intended to be covered by the present invention.

TABLE 1
| Structure | Kinase Assay CDK2/E | IC$_{50}$ (μM) Cell line | | | | | | | | PK | |
|---|---|---|---|---|---|---|---|---|---|---|---|
| | | A2780 | A2780 CisR | CH1 | CH1DoxR | HCT116 | HT29 | KM12 | Average | AUC$_{0-\infty}$ (ng-h/mL) | t$_{1/2}$ (h) |
| 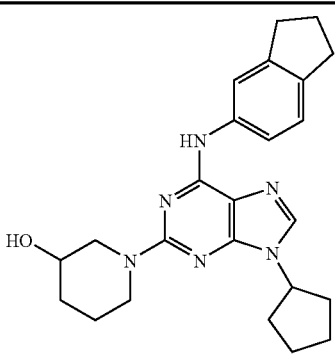 | 0.58 ± 0.33 | 2.2 | 1.1 | 1.5 | 1.7 | 5.7 | 1.8 | 0.34 | 2 | 62489 | 5.5 |
| 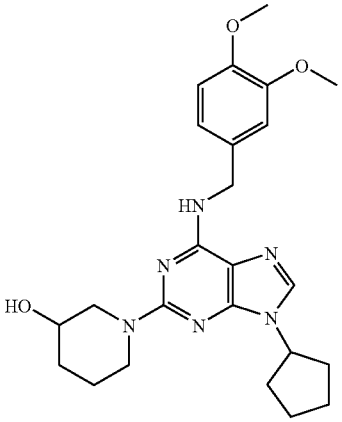 | 1.84 ± 0.31 | 0.078 | 14 | 0.94 | 2.4 | 6.1 | 4.4 | 6.4 | 4.9 | 19493 | 4.2 |
| 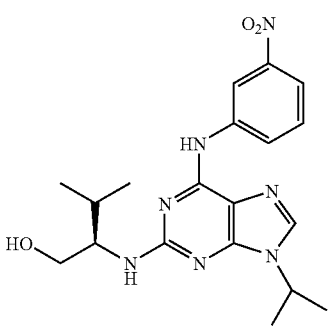 | 0.33 ± 0.45 | 1.1 | 2.85 | 2.3 | 1.8 | 2.45 | 4.3 | 1.05 | 2.3 | | |
| 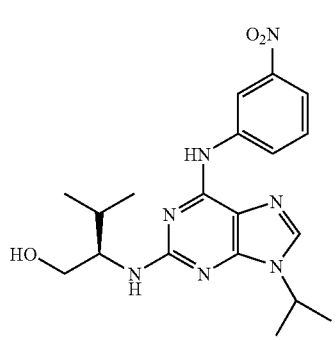 | 0.028 ± 0.01 | 0.245 | 1.7 | 1.1 | 0.56 | 1.2 | 2.1 | 0.76 | 1.1 | | |

TABLE 1-continued

| Structure | IC$_{50}$ (μM) | | | | | | | | | PK | |
| --- | --- | --- | --- | --- | --- | --- | --- | --- | --- | --- | --- |
| | Kinase Assay | Cell line | | | | | | | | | |
| | CDK2/E | A2780 | A2780 CisR | CH1 | CH1DoxR | HCT116 | HT29 | KM12 | Average | AUC$_{0-\infty}$ (ng-h/mL) | t$_{1/2}$ (h) |
| [structure] | 0.26 ± 0.18 | 6.6 | 15 | 17 | 12 | 12 | 15 | 19 | 13.8 | Blocked carbinol metabolism | |
| [structure] | 0.23 ± 0.16 | 6.4 | 3.8 | 5 | 4.6 | 5.4 | 18 | 5.4 | 6.9 | Blocked carbinol metabolism | |
| [structure] | 0.03 ± 0.02 | 3.3 | 3.4 | 1.8 | 1.3 | 1.5 | 5 | 1.9 | 2.6 | Blocked carbinol metabolism | |
| [structure] | 0.06 ± 0.04 | 22 | 28 | 26 | 23 | 26 | 54 | 38 | 31.0 | Improved aqueous solubility | |

TABLE 1-continued

| | IC$_{50}$ (μM) | | | | | | | | | PK | |
|---|---|---|---|---|---|---|---|---|---|---|---|
| | Kinase Assay | Cell line | | | | | | | | | |
| Structure | CDK2/E | A2780 | A2780 CisR | CH1 | CH1DoxR | HCT116 | HT29 | KM12 | Average | AUC$_{0-\infty}$ (ng-h/mL) | t$_{1/2}$ (h) |
| [structure] | 0.48 ± 0.28 | 23 | 22 | 8.2 | 28 | 10 | 23 | 7 | 17.3 | Improved aqueous solubility | |

TABLE 2

[Structure image]

| | Name | | X | Y | Z | R$^a$ | R$^b$ | R$^c$ | R$^d$ |
|---|---|---|---|---|---|---|---|---|---|
| | Roscovitine | 3.7 | CH | CH | CH | Et | H | H | H |
| 7 | (2RS,3R)-3-(6-Benzylamino-9-isopropyl-9H-purin-2-ylamino)-pentan-2-ol | 4.0 | CH | CH | CH | Et | H | Me/H | |
| 5 | (R)-2-Isopropyl-6-(pyridin-2-ylmethyl)-amino]-9H-purin-2-ylamino)-butan-1-ol | 2.2 | N | CH | CH | Et | H | H | H |
| 6 | (R)-2-Isopropyl-6-(pyridin-4-ylmethyl)-amino]-9H-purin-2-ylamino)-butan-1-ol | 2.2 | CH | CH | N | Et | H | H | H |
| 7 | (2RS,3R)-3-(6-Benzylamino-9-isopropyl-9H-purin-2-ylamino)-pentan-2-ol | 4.0 | CH | CH | CH | Et | H | H | Me |
| 7 | (2RS,3R)-3-(6-Benzylamino-9-isopropyl-9H-purin-2-ylamino)-pentan-2-ol | 4.0 | CH | CH | CH | H | Et | Me | H |
| 9 | (3RS,4R)-4-(6-Benzylamino-9-isopropyl-9H-purin-2-ylamino)-hexan-3-ol | 4.5 | CH | CH | CH | Et | H | Et/H | |
| 10 | (3RS,4S)-4-(6-Benzylamino-9-isopropyl-9H-purin-2-ylamino)-hexan-3-ol | 4.5 | CH | CH | CH | H | Et | Et/H | |
| 11 | (3RS,4R)-4-(6-Benzylamino-9-isopropyl-9H-purin-2-ylamino)-2-methyl-hexan-3-ol | 4.9 | CH | CH | CH | Et | H | iPr/H | |
| 12 | (3RS,4S)-4-(6-Benzylamino-9-isopropyl-9H-purin-2-ylamino)-2-methyl-hexan-3-ol | 4.9 | CH | CH | CH | H | Et | iPr/H | |
| 13 | (3RS,4R)-4-(6-Benzylamino-9-isopropyl-9H-purin-2-ylamino)-2,2-dimethyl-hexan-3-ol | 5.3 | CH | CH | CH | Et | H | tBu/H | |
| 14 | (3RS,4S)-4-(6-Benzylamino-9-isopropyl-9H-purin-2-ylamino)-2,2- | 5.3 | CH | CH | CH | H | Et | tBu/H | |
| 15 | (R)-3-(6-Benzylamino-9-isopropyl-9H-purin-2-ylamino)-2-methyl-pentan-2-ol | 4.4 | CH | CH | CH | Et | H | Me | Me |
| 16 | (S)-3-(6-Benzylamino-9-isopropyl-9H-purin-2-ylamino)-2-methyl-pentan-2-ol | 4.4 | CH | CH | CH | H | Et | Me | Me |

TABLE 2-continued

| | Kinase inhibition (μM) | | | | | | | | | | | | In vitro anti-proliferative activity (72-h MTT IC$_{50}$μM) Cell lines: | |
| | CDK2/ cyclin E | | CDK1/ cyclin B | | CDK4/ cyclin D1 | | CDK7/ cyclin H | | PKA | | ERK2 | | A549, HT29, Saos-2 | |
| Example No. | IC$_{50}$ | SD | IC$_{50}$ | SD | IC$_{50}$ | SD | IC$_{50}$ | SD | IC$_{50}$ | SD | IC$_{50}$ | SD | IC$_{50}$ | SD |
|---|---|---|---|---|---|---|---|---|---|---|---|---|---|---|
| | 0.10 | 0.10 | 2.7 | 2.5 | 14 | 4 | 0.49 | 0.26 | >50 | | 1.20 | 1.30 | 12 | 3 |
| 7 | 0.26 | 0.18 | 22 | | 27 | 3 | 1.1 | 0.3 | >50 | | >50 | | 3.9 | 2.3 |
| 5 | 0.06 | 0.04 | 3.9 | 1.00 | 3.8 | 0.4 | 0.04 | 0.02 | >50 | | 9.5 | 0.2 | 4.5 | 3.1 |
| 6 | 0.48 | 0.28 | 28 | | 30 | 5 | 0.74 | 0.09 | >50 | | 32 | | 17 | 2 |
| 7 | 0.23 | 0.16 | 18 | | 23 | 9 | 0.39 | 0.24 | >50 | | 43 | 6 | 8.1 | 3.0 |
| 7 | 0.03 | 0.02 | 9.3 | 8.6 | 9.0 | 5.0 | 0.69 | 0.44 | >50 | | 29 | 3 | 2.2 | 0.4 |
| 9 | 0.73 | 0.25 | 22 | 1 | 34 | 1 | 1.2 | 0.2 | 139 | | 103 | 4 | 11 | 8 |
| 10 | 0.24 | 0.06 | 19 | 7 | 20 | 14 | 1.1 | 0.4 | >200 | | 22 | 17 | 20 | 5 |
| 11 | 2.4 | 1.3 | 28 | 13 | 28 | 8 | 4.4 | 2.1 | 92 | 35 | >200 | | 11 | 11 |
| 12 | 1.8 | 0.4 | 34 | 3 | 33 | 3 | 3.0 | 0.3 | 83 | | 88 | | 28 | 2 |
| 13 | 3.1 | 0.6 | 30 | | >200 | | 3.7 | 0.2 | 87 | | >200 | | 18 | 10 |
| 14 | 1.5 | 0.1 | 45 | 34 | 60 | 23 | 4.3 | 0.2 | >200 | | >200 | | 22 | 10 |
| 15 | 0.38 | 0.31 | 17 | 4 | 12 | 3 | 3.7 | 1.8 | 191 | | 149 | 54 | 15 | 4 |
| 16 | 0.17 | 0.10 | 9.1 | 2.8 | 8.5 | 4 | 2.0 | 0.9 | 200 | | 52 | 59 | 10 | 1 |

The invention claimed is:

1. A compound of formula I

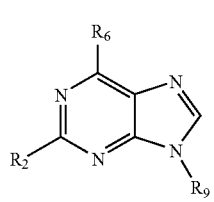

or a pharmaceutically acceptable salt thereof wherein
R$_2$ is 3-hydroxypiperidin-1-yl, or NHCH(R$_4$)CH(R$_3$)OH, wherein R$_3$ is hydrogen or methyl and
R$_4$ is methyl, ethyl or isopropyl;
R$_6$ is 3-nitrophenylamino or indan-5-ylamino; and
R$_9$ is isopropyl or cyclopentanyl.

2. A compound according to claim 1 wherein R$_2$ is NHCH(CHMe$_2$)CH$_2$OH or NHCH(CH$_2$Me)CH$_2$OH.

3. A compound according to claim 1 selected from the following:

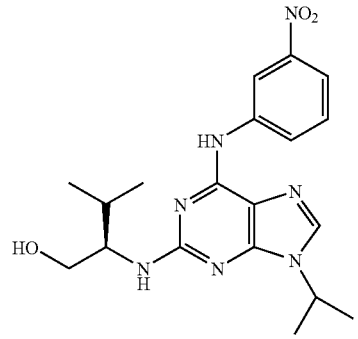

-continued

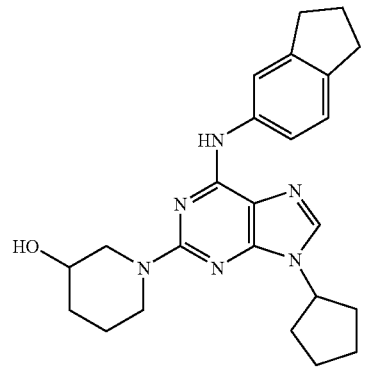

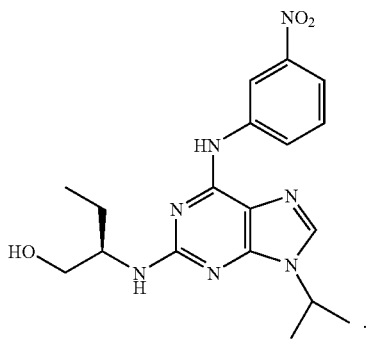

4. A compound selected from the following:

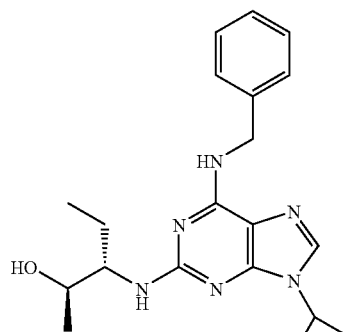

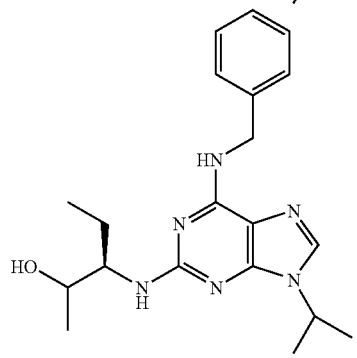

or a pharmaceutically acceptable salt thereof.

5. A compound of formula I

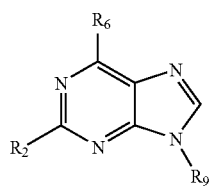

I or a pharmaceutically acceptable salt thereof wherein
  R$_2$ is NHCH(R$_4$)CH(R$_3$)OH, wherein R$_3$ is hydrogen or methyl and R$_4$ is methyl, ethyl or isopropyl;
  R$_6$ is 3,4-dimethoxybenzylamino, pyrid-2-yl-methylamino, or pyrid-4-yl-methylamino; and
  R$_9$ is cyclopentanyl.

6. A compound selected from the following:

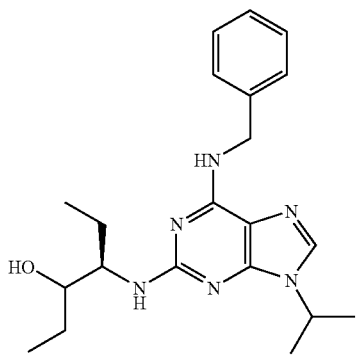

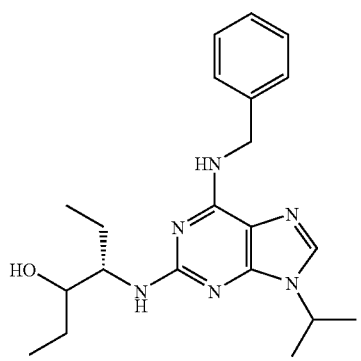

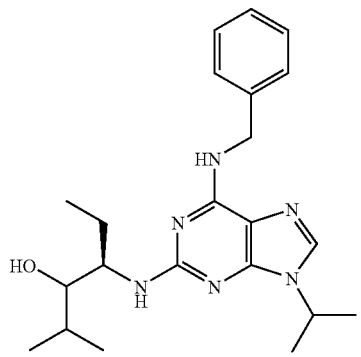

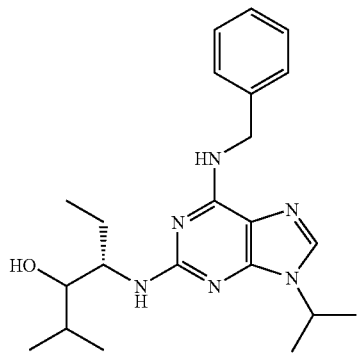

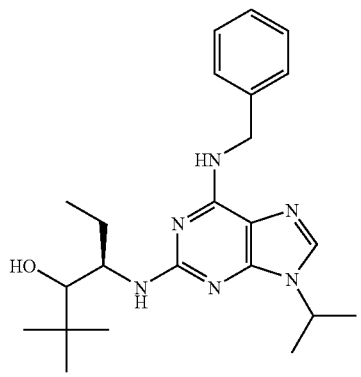

-continued

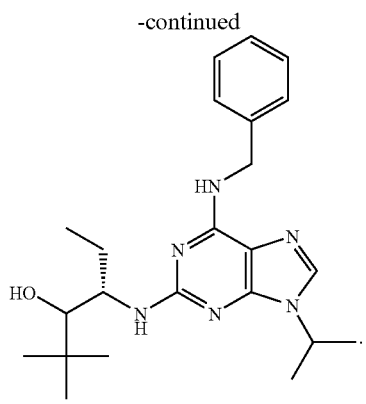

7. A pharmaceutical composition, comprising a compound according to claim 1, 4, 5, or 6 admixed with a pharmaceutically acceptable diluent, excipient or carrier, or a mixture thereof.

8. The pharmaceutical composition of claim 7, wherein said compound is present in an amount sufficient to treat a proliferative disorder.

9. The pharmaceutical composition of claim 8, wherein said proliferative disorder is cancer or leukaemia.

10. The pharmaceutical composition of claim 8, wherein said proliferative disorder is psoriasis.

11. An optical isomer of a compound of claim 1, 4, 5, or 6, wherein said optical isomer is a dextrorotatory (+) isomer.

12. A compound of claim 1, 4, 5, or 6, wherein said compound is in the form of a racemate.

13. The pharmaceutical composition of claim 7, wherein said compound is present in an amount sufficient to treat a neurodegenerative disorder.

14. The pharmaceutical composition of claim 7, wherein said compound is present in an amount sufficient to prevent neuronal apoptosis.

15. The pharmaceutical composition of claim 7, wherein said compound is present in an amount sufficient to be an antiviral agent.

16. The pharmaceutical composition of claim 7, wherein said compound is present in an amount sufficient to be an anti-mitotic agent.

17. The pharmaceutical composition of claim 7, wherein said compound is present in an amount sufficient to inhibit at least one of CDK2, CDK7, CDK8, or CDK9.

18. A method of treating cancer, said method comprising administering to a mammal a therapeutically effective amount of a compound according to claim 1, 4, 5, or 6, such that said cancer is treated, wherein said cancer is an ovarian carcinoma.

19. The method according to claim 18, wherein said compound is administered orally.

20. A method of inhibiting a cyclin dependent kinase, said method comprising contacting said cyclin dependent kinase with a compound according to claim 1, 4, 5, or 6, such that said cyclin dependent kinase is inhibited, and wherein said cyclin dependent kinase is CDK2, CDK7, or CDK9.

21. The method according to claim 20, wherein said cyclin dependent kinase is CDK2.

22. An optical isomer of a compound of claim 1, 4, 5, or 6, wherein said optical isomer is a laevorotatory (−) isomer.

* * * * *